United States Patent
Hoque et al.

(10) Patent No.: US 9,187,786 B2
(45) Date of Patent: Nov. 17, 2015

(54) OVARIAN CANCER METHYLOME

(75) Inventors: Mohammad O. Hoque, Towson, MD (US); Mariana Brait, Baltimore, MD (US); Leonel Maldonado, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 264 days.

(21) Appl. No.: 13/203,480

(22) PCT Filed: Feb. 26, 2010

(86) PCT No.: PCT/US2010/025661
§ 371 (c)(1),
(2), (4) Date: Sep. 28, 2011

(87) PCT Pub. No.: WO2010/099489
PCT Pub. Date: Sep. 2, 2010

(65) Prior Publication Data
US 2012/0014871 A1    Jan. 19, 2012

Related U.S. Application Data

(60) Provisional application No. 61/179,777, filed on May 20, 2009, provisional application No. 61/156,218, filed on Feb. 27, 2009.

(51) Int. Cl.
*C12Q 1/68* (2006.01)
*C07H 21/04* (2006.01)

(52) U.S. Cl.
CPC ........ *C12Q 1/6886* (2013.01); *C12Q 2523/125* (2013.01); *C12Q 2600/106* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

2007/0184438 A1* 8/2007 Lofton-Day et al. ............ 435/6
2008/0032292 A1   2/2008 Cairns

OTHER PUBLICATIONS

Okochi-Takada, E. et al. Int. J. Cancer 119:1338 (Sep. 2006).*
Imura et al., "Methylation and Expression Analysis of 15 Genes and Three Normally-Methylated Genes in 13 Ovarian Cancer Cell Lines," *Cancer Lett.* (2006), 241:213-220, Suppl. (1 page).
Makarla et al., "Promoter Hypermethylation Profile of Ovarian Epithelial Neoplasms," *Clin. Cancer Res.* (2005), 11(15):5365-5369, American Association for Cancer Research.
Rathi et al., "Methylation Profiles of Sporadic Ovarian Tumors and Nonmalignant Ovaries from High-Risk Women," *Clin. Cancer Res.* (2002), 8(11):3324-3331, American Association for Cancer Research.
Barton et al., "DNA methylation changes in ovarian cancer: implications for early diagnosis, prognosis and treatment", *Gynecol. Oncol.*, Apr. 2008;109(1):129-39. Epub Jan. 29, 2008.

(Continued)

*Primary Examiner* — Diana B Johannsen
(74) *Attorney, Agent, or Firm* — DLA Piper LLP (US)

(57) ABSTRACT

The present invention provides methods and kits for identifying a cell that exhibits or is predisposed to exhibiting unregulated growth by detecting hypermethylation of a gene or a regulatory region in at least one gene in the cell. Also provided are methods for diagnosis or prognosis of ovarian cancer in a subject. Also provided are methods of ameliorating ovarian cancer in a subject by administering to the subject an agent that demethylates a hypermethylated gene or regulatory region thereof.

26 Claims, 15 Drawing Sheets

(56) References Cited

OTHER PUBLICATIONS

Brait et al., "Ovarian cancer methylome and its potential as biomarker", *Proc. Am. Assoc. Cancer Res.*; 100th AACR Annual Meeting—Apr. 18-22, 2009; Denver, CO. Abstract No. 3361.

Chakraborty et al., "Identification of genes associated with tumorigenesis of retinoblastoma by microarray analysis", *Genomics*, Sep. 2007;90(3):344-53. Epub Jun. 29, 2007.

Maldonado et al., "GULP1, a potential tumor suppressor gene in ovarian tumors and its utility as a biomarker", *Proceedings of the American Association for Cancer Research Annual Meeting*, Abstract No. 4891, vol. 51, p. 1189 (2010).

Ronchetti et al., "An integrative genomic approach reveals coordinated expression of intronic miR-335, miR-342, and miR-561 with deregulated host genes in multiple myeloma", *BMC Medical Genomics*, Aug. 13, 2008, 1:37.

Tam et al., "Methylation profile in benign, borderline and malignant ovarian tumors", *J. Cancer Res. Clin. Oncol.*, May 2007;133(5):331-41. Epub Dec. 20, 2006.

* cited by examiner

CANDIDATE APPROACH
Genes known to be inactivated
by METHYLATION
in Cancer
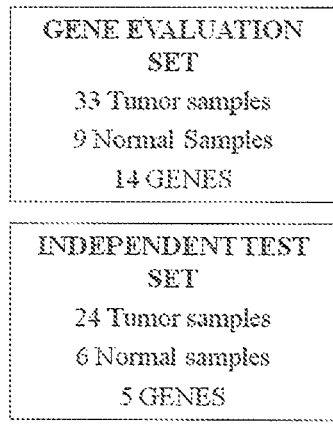
FIG. 2A
Quantitative Methylation Specific PCR
(QMSP)
DNA extraction from the tissue
Sodium Bisulfite Treatment of DNA
Real time PCR
Data analysis
Statistical Analysis
FIG. 2B

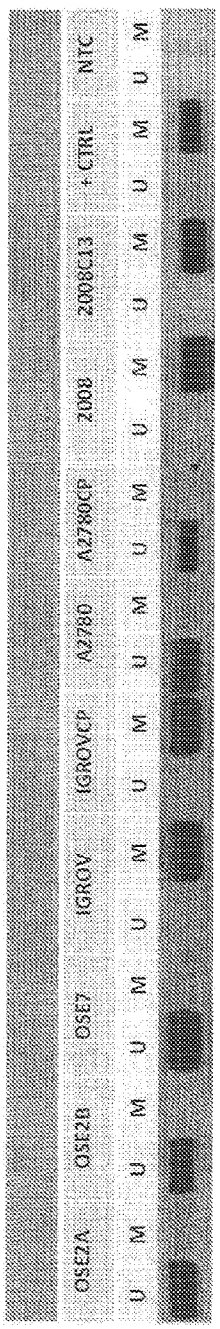
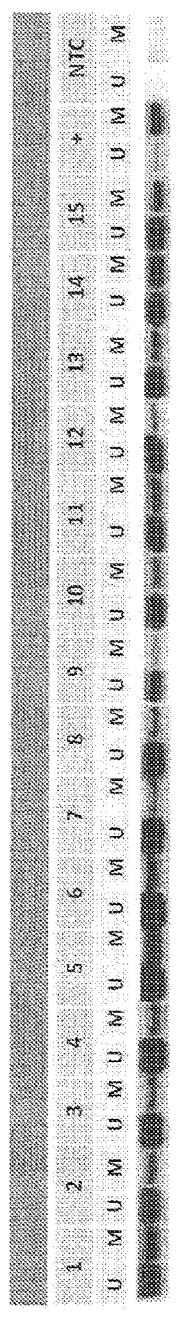
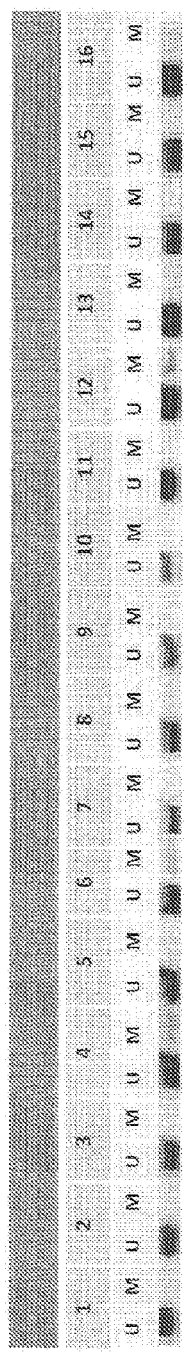
FIG. 15A                    FIG. 15B                    FIG. 15C

OVARIAN CANCER METHYLOME

CROSS REFERENCE TO RELATED APPLICATIONS

This application is a 35 USC §371 National Stage application of International Application No. PCT/US2010/025661 filed Feb. 26, 2010, now pending; which claims the benefit under 35 USC §119(e) to U.S. application Ser. No. 61/179,777 filed May 20, 2009 and to U.S. application Ser. No. 61/156,218 filed Feb. 27, 2009, both now expired. The disclosure of each of the prior applications is considered part of and is incorporated by reference in the disclosure of this application.

BACKGROUND OF THE INVENTION

1. Field of the Invention

The invention relates generally to methods and kits useful for detecting, diagnosing or evaluating cancer and more specifically to methods and kits for detecting, diagnosing or evaluating ovarian cancer by detecting methylation changes in nucleic acid samples of subjects with a profile of gene markers.

2. Background Information

Ovarian cancer is the second most common gynecological cancer and the leading cause of death among gynecological cancers worldwide. Approximately 21,650 new cases were detected in 2008 in the United States, leading to approximately 15,520 deaths from this cancer. Seventy percent of patients with ovarian cancer have advanced disease (stage III or IV) at presentation, with a 5-year survival rate of 15 to 20% despite aggressive treatment, while patients presenting with early disease have a survival rate above 90%. The high mortality of ovarian cancer is related to the absence of symptoms in the majority of the cases during the early stages of the disease, and also to the lack of truly sensitive and specific screening techniques. The best studied serum biomarker for ovarian cancer is CA-125, which is elevated in approximately 80% of women with advanced disease, but only 50-60% in patients with early-stage disease.

It has been shown that genetic and epigenetic changes contribute to the development and progression of tumor cells. Epigenetic alterations in promoter methylation and histone acetylation have been associated with cancer-specific expression differences in human malignancies. Methylation has been primarily considered as a mechanism of tumor suppressor gene (TSG) inactivation, and comprehensive whole-genome profiling approaches to promoter hypermethylation have identified multiple novel putative TSGs silenced by promoter hypermethylation.

Understanding the epigenetic changes that lead to cancer progression will help unravel key biologic processes that lead to cancer formation. Thus, there is an imperative need to find new molecular markers that will: a) help determine the risk of developing cancer to consider appropriate preventive interventions; b) help detect cancers early when they are amenable to surgical cure; c) help to predict response of a particular therapy (such as paclitaxel); and d) help to determine the overall outcome of a cancer patient.

SUMMARY OF THE INVENTION

The present invention is based on the discovery that some genes have promoters that are hypermethylated in cancer. As a result, typically the gene expression is down-regulated. This discovery is useful for cancer screening, risk-assessment, prognosis, and identification of subjects responsive to a therapeutic regimen. Accordingly, there are provided methods for detecting a cellular proliferative disorder (e.g., ovarian cancer) in a subject. The methods of the invention are useful for diagnostic, prognostic as well therapeutic prediction.

In one aspect, the invention provides a method for diagnosing ovarian cancer in a subject having or at risk of developing ovarian cancer. The method includes determining the methylation state of a gene or a regulatory region of a gene in at least two genes. By way of example, such genes may include at least one gene selected from the group consisting of GULP1, CSGALNACT2, PGP9.5, HIC1, AIM1, APC, PAK3, MCAM, MGMT, KIF1A, CCNA1, ESR1, SSBP2, GSTP1, FKBP4, VGF, and any combination thereof, in a nucleic acid sample from the subject. A hypermethylated state, as compared to a corresponding normal cell, is indicative of a subject having or at risk of developing ovarian cancer. In one embodiment, at least two genes or regulatory regions are hypermethylated and the at least two genes are coordinately silenced in the cell undergoing unregulated cell growth. In another embodiment, the method includes contacting a nucleic acid-containing sample from cells of the subject with an agent that provides a determination of the methylation state of at least one gene or at least one regulatory region of a gene, wherein the at least one regulatory region is hypermethylated in a cell undergoing unregulated cell growth as compared to a corresponding normal cell; and identifying hypermethylation of the regulatory region in the nucleic acid-containing sample, as compared to the same region of the at least one regulatory region in a subject not having ovarian cancer, wherein hypermethylation is indicative of a subject having or at risk of developing ovarian cancer.

In another aspect, the invention provides a method for diagnosing cancer in a subject having or at risk of developing a cell proliferative disorder. The method includes determining the methylation state of at least one gene or a regulatory region of the at least one gene. By way of example, such genes may include at least one gene selected from the group consisting of GULP1 and CSGALNACT2, in a nucleic acid sample from the subject. A hypermethylated state, as compared to a corresponding normal cell, is indicative of a subject having or at risk of developing a cell proliferative disorder. In one embodiment, at least two genes or regulatory regions are hypermethylated and the at least two genes are coordinately silenced in the cell undergoing unregulated cell growth. In another embodiment, the method includes contacting a nucleic acid-containing sample from cells of the subject with an agent that provides a determination of the methylation state of at least one gene or at least one regulatory region of a gene, wherein the at least one regulatory region is hypermethylated in a cell undergoing unregulated cell growth as compared to a corresponding normal cell; and identifying hypermethylation of the regulatory region in the nucleic acid-containing sample, as compared to the same region of the at least one regulatory region in a subject not having ovarian cancer, wherein hypermethylation is indicative of a subject having or at risk of developing a cell proliferative disorder.

In another aspect, the invention provides a method of determining the prognosis of a subject having ovarian cancer. The method includes determining the methylation state of a gene or a regulatory region of a gene in at least two genes. By way of example, such genes may include at least one gene selected from the group consisting of GULP1, CSGALNACT2, PGP9.5, HIC1, AIM1, APC, PAK3, MCAM, MGMT, KIF1A, CCNA1, ESR1, SSBP2, GSTP1, FKBP4, VGF, and any combination thereof, in a nucleic acid sample from the subject. A hypermethylated state, as compared to a corresponding normal cell in the subject or a subject not having the disorder, is indicative of a poor prognosis. In one embodiment, at least two genes or regulatory regions are hypermethylated and the at least two genes are coordinately silenced in the cell undergoing unregulated cell growth.

In another aspect, the invention provides a method of determining the prognosis of a subject having cancer. The method includes determining the methylation state of at least one gene or a regulatory region thereof. By way of example, such genes may include at least one gene selected from the group consisting of GULP1 and CSGALNACT2, in a nucleic acid sample from the subject. A hypermethylated state, as compared to a corresponding normal cell in the subject or a subject not having the disorder, is indicative of a poor prognosis. In one embodiment, at least two genes or regulatory regions are hypermethylated and the at least two genes are coordinately silenced in the cell undergoing unregulated cell growth.

In another aspect, the invention provides a method of ameliorating symptoms associated with ovarian cancer in a subject in need thereof. The method includes administering to the subject an agent that demethylates at least one gene or regulatory region of a gene. By way of example, such genes may include at least one gene selected from the group consisting of GULP1, CSGALNACT2, PGP9.5, HIC1, AIM1, APC, PAK3, MCAM, MGMT, KIF1A, CCNA1, ESR1, SSBP2, GSTP1, FKBP4, VGF, and any combination thereof. Demethylation of the at least one gene or regulatory region of a gene that is in a hypermethylated state, as compared to that of a subject not having ovarian cancer, increases expression of the at least one gene or regulatory region, thereby ameliorating the symptoms associated with ovarian cancer. In one embodiment, at least two genes or regulatory regions are hypermethylated and the at least two genes are coordinately silenced in the cell undergoing unregulated cell growth.

In another aspect, the invention provides a method of ameliorating a cell proliferative disorder in a subject in need thereof. The method includes administering to the subject an agent that demethylates at least one gene or regulatory region of a gene. By way of example, such genes may include at least one gene selected from the group consisting of GULP1 and CSGALNACT2. Demethylation of the at least one gene or regulatory region of a gene that is in a hypermethylated state, as compared to that of a subject not having ovarian cancer, increases expression of the at least one gene or regulatory region, thereby ameliorating the symptoms associated with ovarian cancer. In one embodiment, at least two genes or regulatory regions are hypermethylated and the at least two genes are coordinately silenced in the cell undergoing unregulated cell growth.

In another aspect, the invention provides a method for determining whether a subject is responsive to a particular therapeutic regimen. The method includes determining the methylation state of a gene or a regulatory region of a gene in at least two genes. In another embodiment, the method includes determining the methylation state of at least one gene or a regulatory region thereof. By way of example, such genes may include at least one gene selected from the group consisting of GULP1, CSGALNACT2, PGP9.5, HIC1, AIM1, APC, PAK3, MCAM, MGMT, KIF1A, CCNA1, ESR1, SSBP2, GSTP1, FKBP4, VGF, and any combination thereof. In another embodiment, the genes include at least one gene selected from the group consisting of GULP1 and CSGALNACT2. A hypermethylated state of the one or more genes or regulatory regions thereof, as compared with that of a normal subject, is indicative of a subject who is responsive to the therapeutic regimen. In one embodiment, the therapeutic regimen is administration of one or more chemotherapeutic agents alone or in combination with one or more demethylating agents such as, but not limited to, 5-azacytidine, 5-aza-2-deoxycytidine and zebularine. In another embodiment, the therapeutic regimen is administration of cisplatin in combination with paclitaxel.

In another aspect, the invention provides a method for identifying a cell that exhibits or is predisposed to exhibiting unregulated growth. The method includes detecting hypermethylation of a gene or regulatory region of a gene in at least two genes. By way of example, such genes may include at least one gene selected from the group consisting of GULP1, CSGALNACT2, PGP9.5, HIC1, AIM1, APC, PAK3, MCAM, MGMT, KIF1A, CCNA1, ESR1, SSBP2, GSTP1, FKBP4, VGF, and any combination thereof. A hypermethylated state of the one or more genes or regulatory regions thereof, as compared to a corresponding normal cell not exhibiting unregulated growth, identifies the cell as exhibiting or predisposed to exhibiting unregulated growth. In one embodiment, at least two genes or regulatory regions are hypermethylated and the at least two genes are coordinately silenced in the cell undergoing unregulated cell growth. In another embodiment, the cell exhibiting, or predisposed to exhibiting unregulated growth is a cancer cell, such as an ovarian cancer cell.

In another aspect, the invention provides a method for identifying a cell that exhibits or is predisposed to exhibiting unregulated growth. The method includes detecting hypermethylation of a gene or a regulatory region thereof. By way of example, such genes may include at least one gene selected from the group consisting of GULP1 and CSGALNACT2. A hypermethylated state of the one or more genes or regulatory regions thereof, as compared to a corresponding normal cell not exhibiting unregulated growth, identifies the cell as exhibiting or predisposed to exhibiting unregulated growth. In one embodiment, at least two genes or regulatory regions are hypermethylated and the at least two genes are coordinately silenced in the cell undergoing unregulated cell growth. In another embodiment, the cell exhibiting, or predisposed to exhibiting unregulated growth is a cancer cell, such as an ovarian cancer cell, a testicular cancer cell, or a bladder cancer cell.

In another aspect, the invention provides a kit useful for the detection of a methylated CpG-containing nucleic acid in determining the methylation status of one or more genes or regulatory regions thereof. By way of example, such genes may include at least one gene selected from the group consisting of GULP1, CSGALNACT2, PGP9.5, HIC1, AIM1, APC, PAK3, MCAM, MGMT, KIF1A, CCNA1, ESR1, SSBP2, GSTP1, FKBP4, VGF, and any combination thereof. In one embodiment, the kit includes a carrier element containing one or more containers comprising a first container containing a reagent that modifies unmethylated cytosine and a second container containing primers for amplification of the one or more genes or regulatory regions thereof, wherein the primers distinguish between modified methylated and unmethylated nucleic acid. In another embodiment, the kit further includes a panel of two or more genes selected from the group consisting of GULP 1, CSGALNACT2, PGP9.5, HIC1, AIM1, APC, PAK3, MCAM, MGMT, KIF1A, CCNA1, ESR1, SSBP2, GSTP1, FKBP4, VGF, and any combination thereof.

BRIEF DESCRIPTION OF THE DRAWINGS

FIGS. 2A and 2B are pictorial diagrams showing another gene selection flow chart for testing of genes regulated by promoter methylation in ovarian cancer (Candidate Approach). FIG. 2A shows the Samples set for Candidate Approach Analyses. FIG. 2B shows a flowchart of Analyses with Quantitative Methylation Specific PCR (QMSP).

FIGS. 15A-15C are pictorial diagrams showing promoter methylation of GULP1. FIG. 15A shows methylation of GULP1 by conventional methylation-specific PCR in cancer cell lines (IGROV, A2780, 2008), and normal cell lines (OSE2A, OSE2B, OSE7); M, methylated; U, unmethylated; NTC, no template control; +CTRL, positive control (100% in vitro methylated DNA). FIG. 15B shows primary ovarian tumors. FIG. 15C shows normal ovarian tissues.

DETAILED DESCRIPTION OF THE INVENTION

Figure 1:
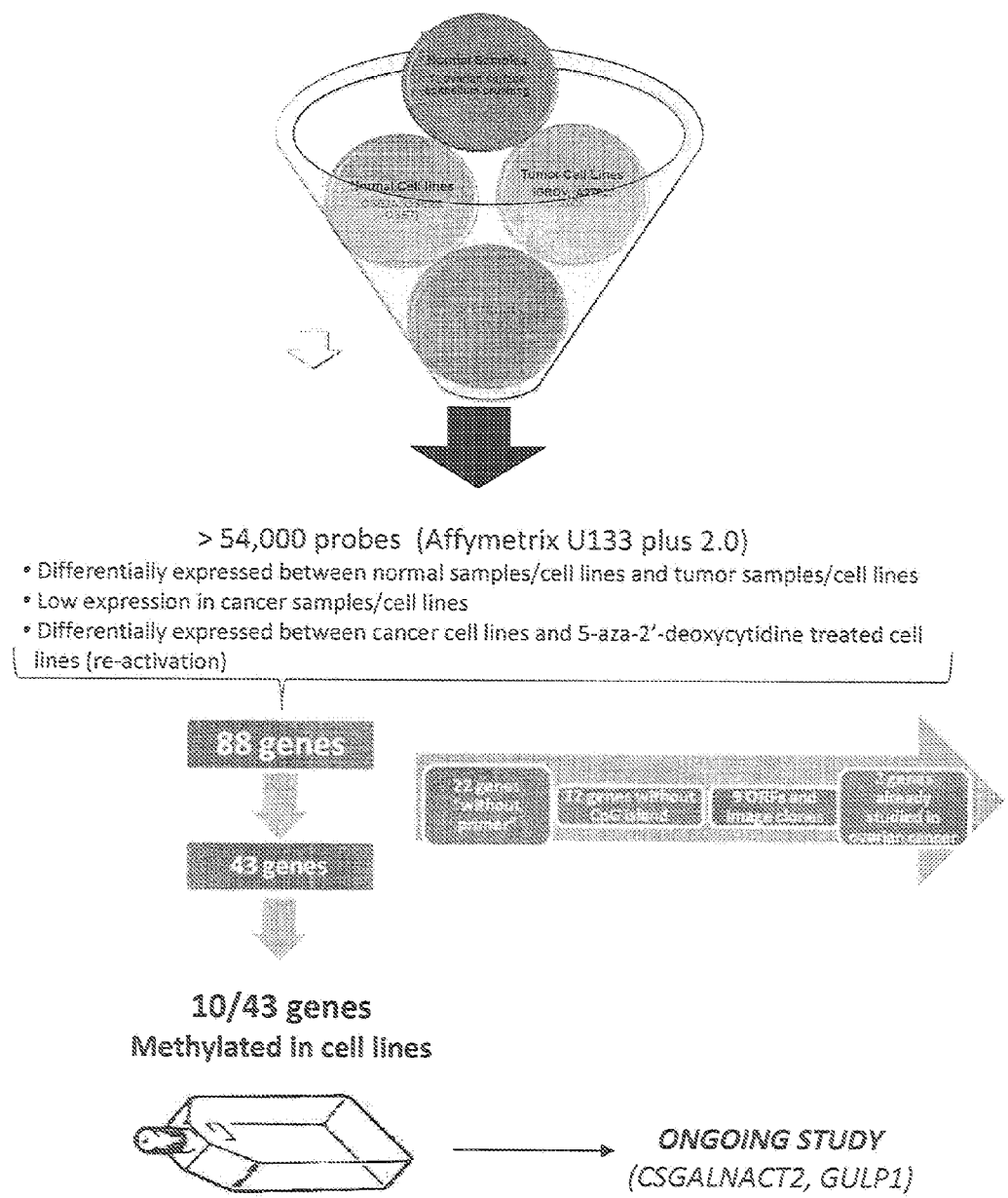
FIG. 1 is a pictorial diagram showing a gene selection flow chart for discovery of genes regulated by promoter methylation in ovarian cancer (Discovery Approach).
Figure 3:
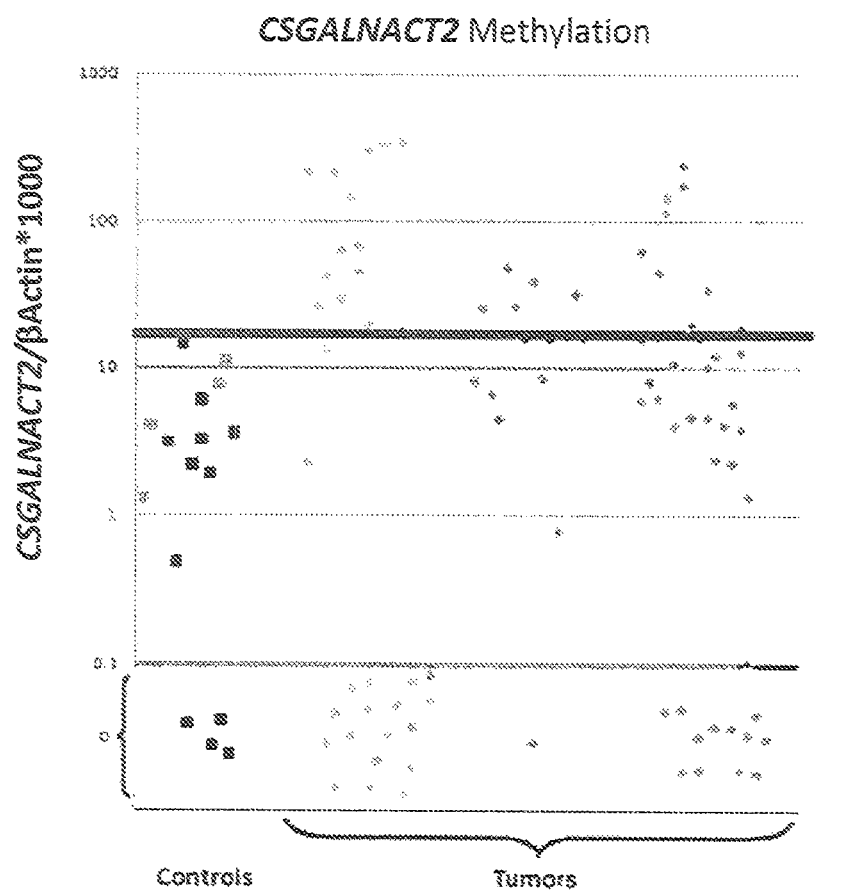
FIG. 3 is a graphical diagram showing promoter methylation levels for the CSGALNACT2 gene in the ovarian cancer patient samples (Tumors; n=57) and normal ovary tissues (Controls; n=15). The quantity of each methylated gene promoter was expressed as the ratio of the amount of PCR products amplified from the methylated gene to the amount amplified with the reference gene β-actin multiplied by 1,000.
Figure 4:
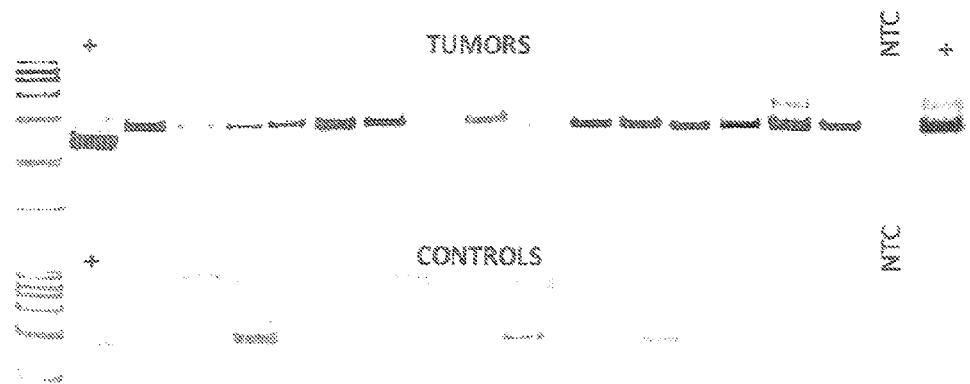
FIG. 4 is a pictorial diagram showing results of a conventional methylation specific PCR. PCR products were electrophoresed on a 8% polyacrilamide gel for the detection of promoter methylation in the GULP1 gene in the ovarian cancer patient samples (Tumors) and normal ovary tissues (Controls). The amplicon size is 169 bp. NTC, no template control; +CTRL, positive control (100% in vitro methylated DNA).
Figure 5:
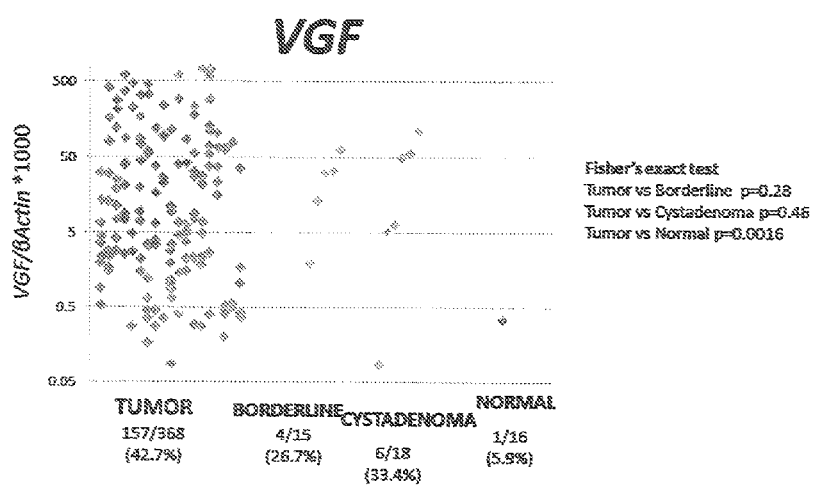
FIG. 5 is a graphical diagram showing promoter methylation levels for the VGF gene in the ovarian cancer patient samples (Tumors; n=368, borderline tumors; n=15), benign tumors (cystadenoma; n=18) and normal ovary tissues (Controls; n=16). The quantity of each methylated gene promoter was expressed as the ratio of the amount of PCR products amplified from the methylated gene to the amount amplified with the reference gene β-actin multiplied by 1,000.
Figure 6:
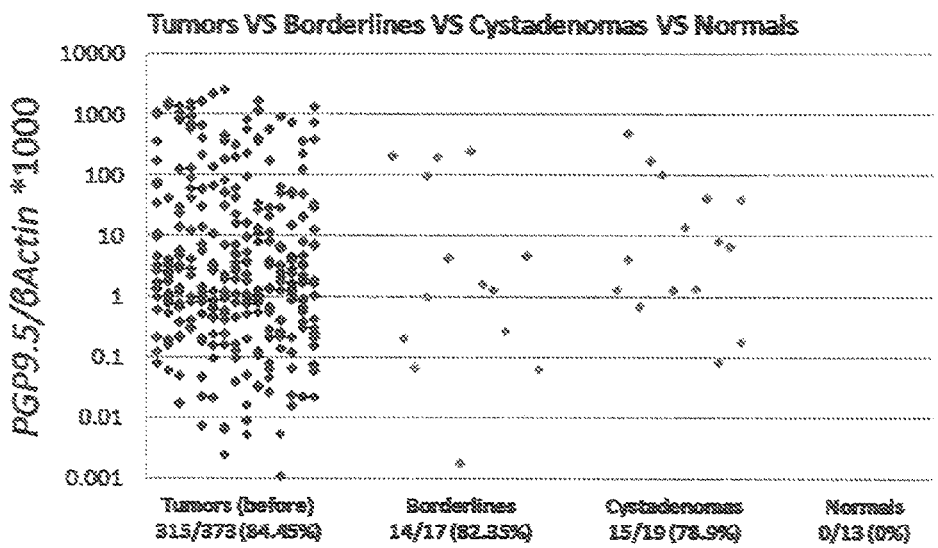
FIG. 6 is a graphical diagram showing promoter methylation levels for the PGP9.5 gene in the ovarian cancer patient samples (Tumors; n=373, borderline tumors; n=17), benign tumors (cystadenoma; n=19) and normal ovarian tissues (Controls; n=13). The quantity of each methylated gene promoter was expressed as the ratio of the amount of PCR products amplified from the methylated gene to the amount amplified with the reference gene β-actin multiplied by 1,000.
Figure 7:
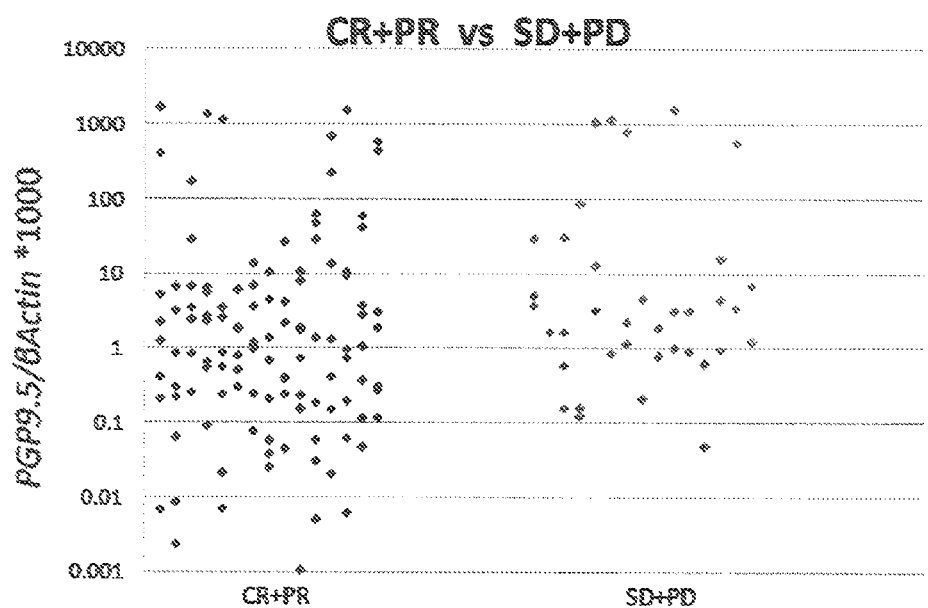
FIG. 7 is a graphical diagram showing promoter methylation levels for the PGP9.5 gene in the ovarian cancer patient samples divided in 2 groups the ones that responded to chemotherapy treatment (CR+PR; n=144) and the ones that did not respond (SD+PD, n=55). The quantity of each methylated gene promoter was expressed as the ratio of the amount of PCR products amplified from the methylated gene to the amount amplified with the reference gene β-actin multiplied by 1,000.
Figure 8:
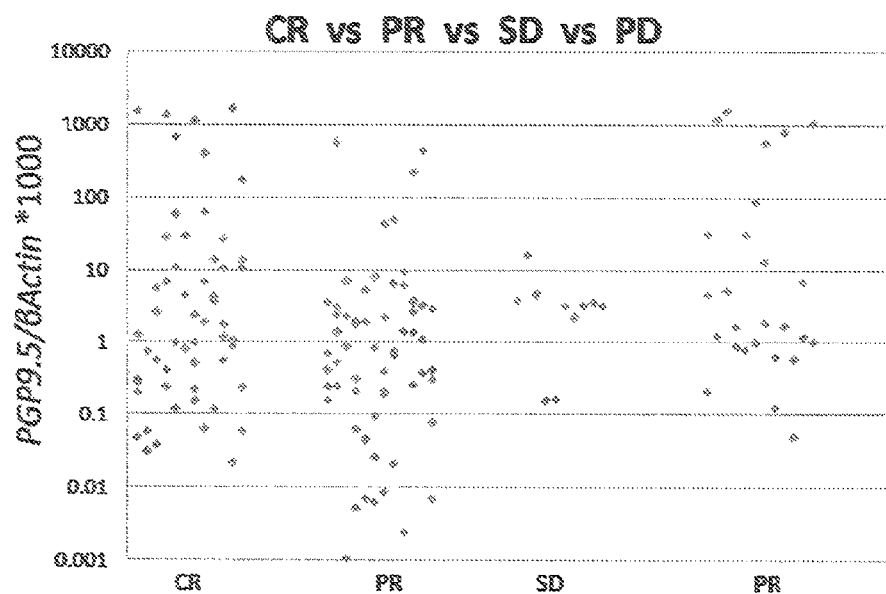
FIG. 8 is a graphical diagram showing promoter methylation levels for the PGP9.5 gene in the ovarian cancer patient samples subdivided in 4 groups the ones that responded to chemotherapy treatment in complete response (CR; n=68) and partial response (PR; n=76) and the ones that did not respond: Stable disease (SD; n=17), and progressive disease (PD; n=38). The quantity of each, methylated gene promoter was expressed as the ratio of the amount of PCR products amplified from the methylated gene to the amount amplified with the reference gene β-actin multiplied by 1,000.
Figure 9:
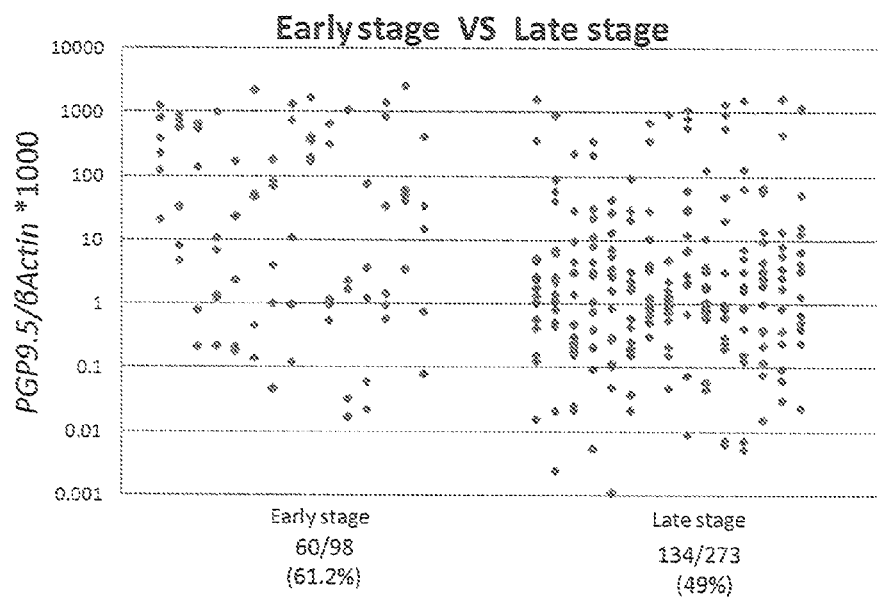
FIG. 9 is a graphical diagram showing promoter methylation levels for the PGP9.5 gene in the ovarian cancer patient samples divided by stage (Early Stage; n=98 and Late Stage; n=273). The quantity of each methylated gene promoter was expressed as the ratio of the amount of PCR products amplified from the methylated gene to the amount amplified with the reference gene β-actin multiplied by 1,000. 61.2% of the early stage patients showed methylation and 49% of the late stage patients showed methylation.
Figure 10:
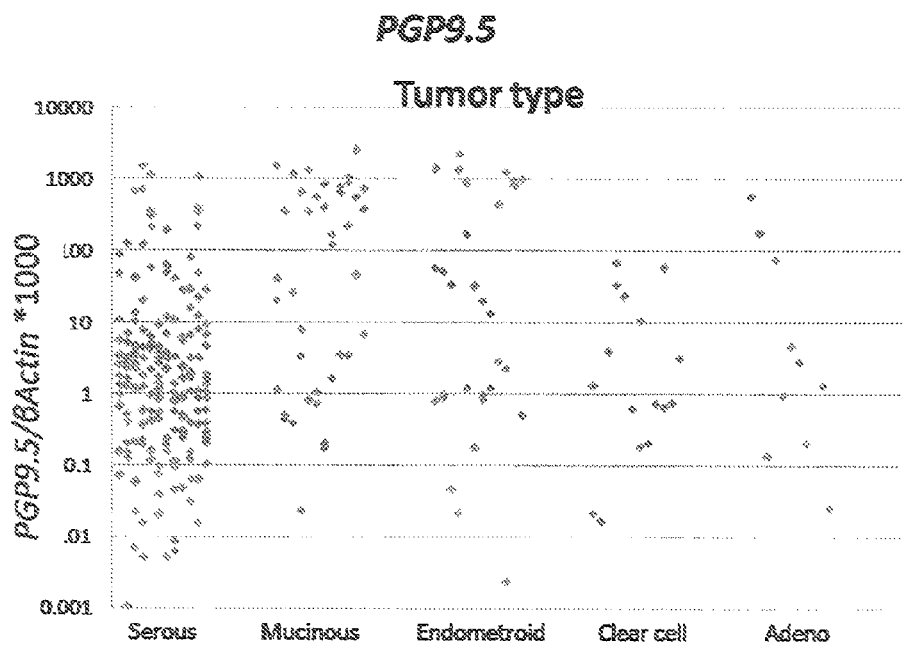
FIG. 10 is a graphical diagram showing promoter methylation levels for the PGP9.5 gene in the ovarian cancer patient samples of different histology; Serous (n=245), Mucinous (n=43), Endometrioid (n=39), Clear Cell (n=20), Adeno (n=15). The quantity of each methylated gene promoter was expressed as the ratio of the amount of PCR products amplified from the methylated gene to the amount amplified with the reference gene β-actin multiplied by 1,000.
Figure 11:
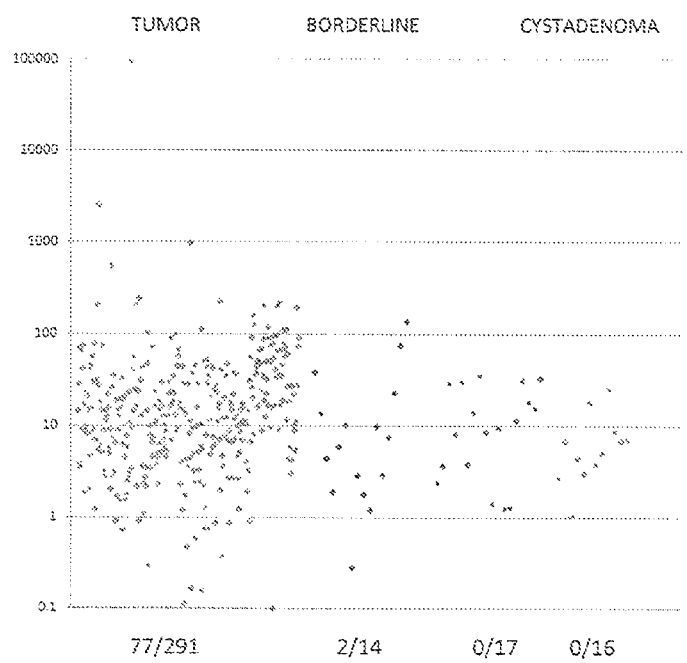
FIG. 11 is a graphical diagram showing promoter methylation levels for the CSGALNACT2 gene in the ovarian cancer patient samples (Tumors; n=291, borderline tumors; n=14), benign tumors (cystadenoma; n=17) and normal ovary tissues (Controls; n=16). The quantity of each methylated gene promoter was expressed as the ratio of the amount of PCR products amplified from the methylated gene to the amount amplified with the reference gene β-actin multiplied by 1,000.
Figure 12:
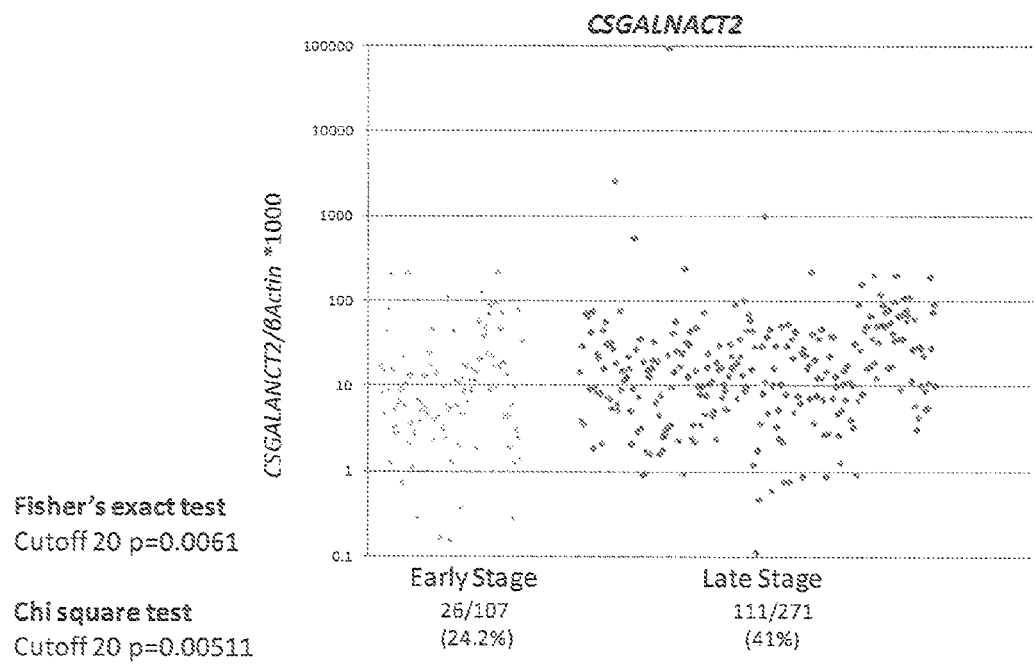
FIG. 12 is a graphical diagram showing promoter methylation levels for the CSGALNACT2 gene in the ovarian cancer patient samples divided by stage (Early Stage; n=107 and Late Stage; n=271). The quantity of each methylated gene promoter was expressed as the ratio of the amount of PCR products amplified from the methylated gene to the amount amplified with the reference gene β-actin multiplied by 1,000.
Figure 13:
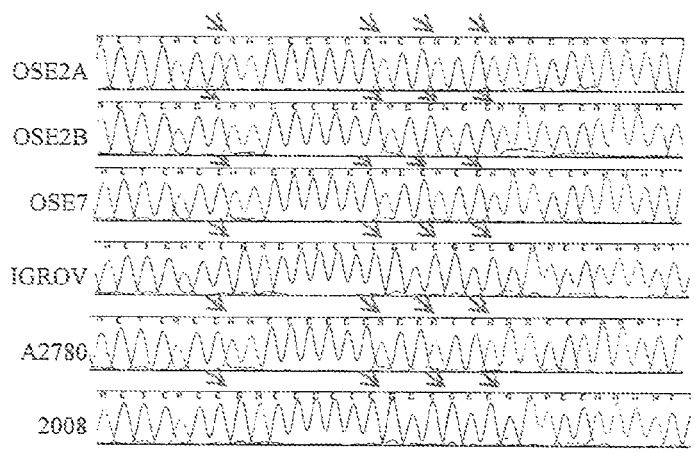
FIG. 13 is a pictorial diagram showing representative sequencing results of the GULP1 gene in cancer cell lines (IGROV, A2780, 2008), and normal cell lines (OSE2A, OSE2B, OSE7). Arrows, all guanines present after sequencing are complementary to methyl cytosines on the opposite DNA strand. The adenines are complementary to timines, representing absence of methylation.
Figure 14:
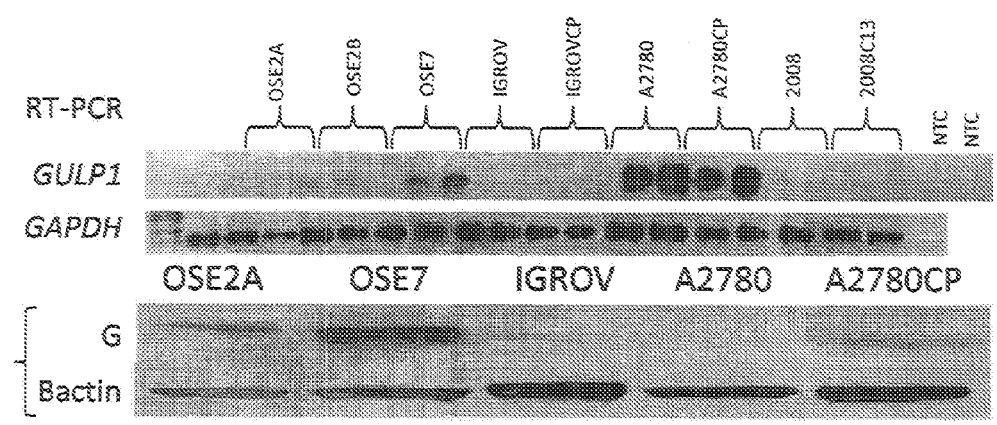
FIG. 14 is a pictorial diagram showing GULP1 expression in normal cell lines (OSE2A, OSE2B, OSE7) and cancer cell lines (IGROV, A2780, 2008). Top=RT-PCR to assess RNA level. Bottom=Western blot to assess protein level.
Figure 16:
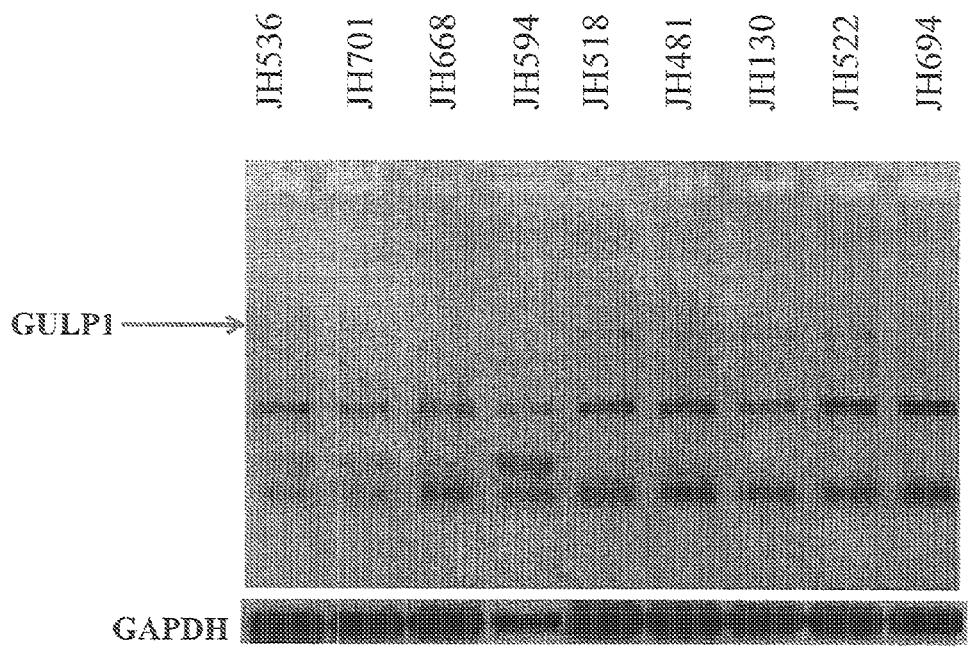
FIG. 16 is a pictorial diagram showing GULP1 expression in primary ovarian tumors. RT-PCR to assess RNA level.
Figure 17:
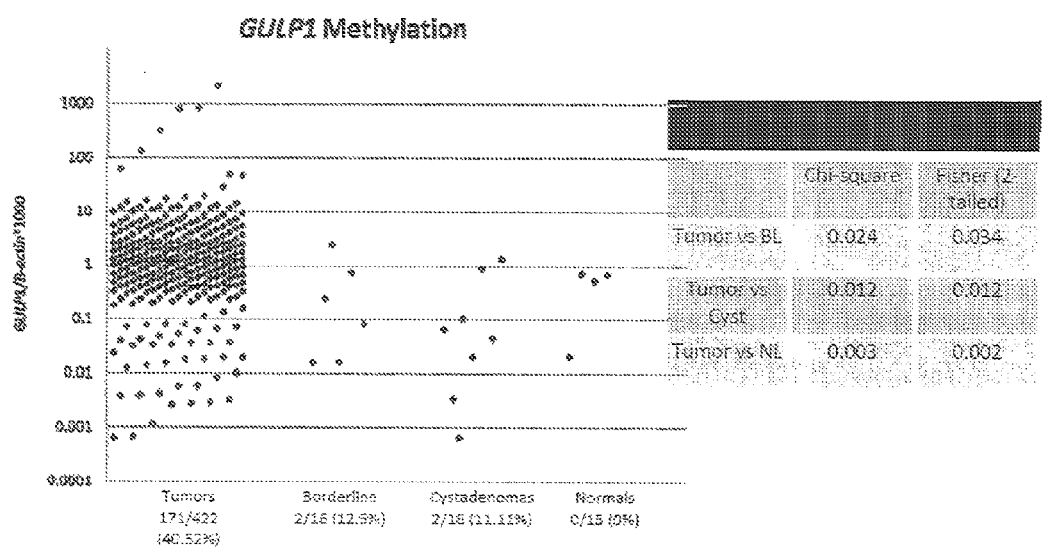
FIG. 17 is a graphical diagram showing promoter methylation levels for the GULP1 gene in the ovarian tumor samples of different histology (Tumors; n=422, borderline tumors; n=16), benign tumors (cystadenoma; n=18) and normal ovary tissues (Controls; n=13). The quantity of each methylated gene promoter was expressed as the ratio of the amount of PCR products amplified from the methylated gene to the amount amplified with the reference gene β-actin multiplied by 1,000.
Figure 18:
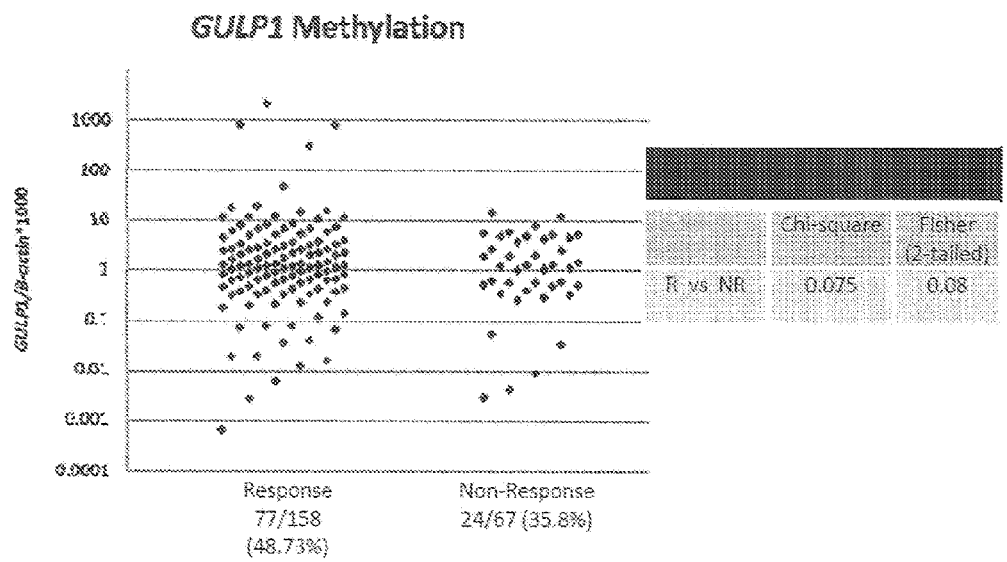
FIG. 18 is a graphical diagram showing promoter methylation levels for the GULP1 gene in the ovarian cancer patient samples divided into two groups, the ones that responded to chemotherapy treatment (n=158) and the ones that did not respond (n=67). The quantity of each methylated gene promoter was expressed as the ratio of the amount of PCR products amplified from the methylated gene to the amount amplified with the reference gene β-actin multiplied by 1,000.
Figure 19:
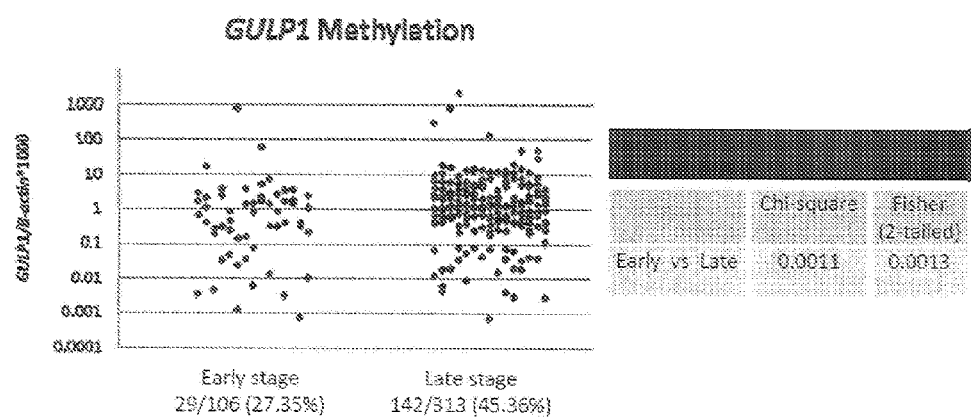
FIG. 19 is a graphical diagram showing promoter methylation levels for the GULP1 gene in the ovarian cancer patient samples stratified by stage (Early Stage; n=106 and Late Stage; n=313). The quantity of each methylated gene promoter was expressed as the ratio of the amount of PCR products amplified from the methylated gene to the amount amplified with the reference gene β-actin multiplied by 1,000.
Figure 20:
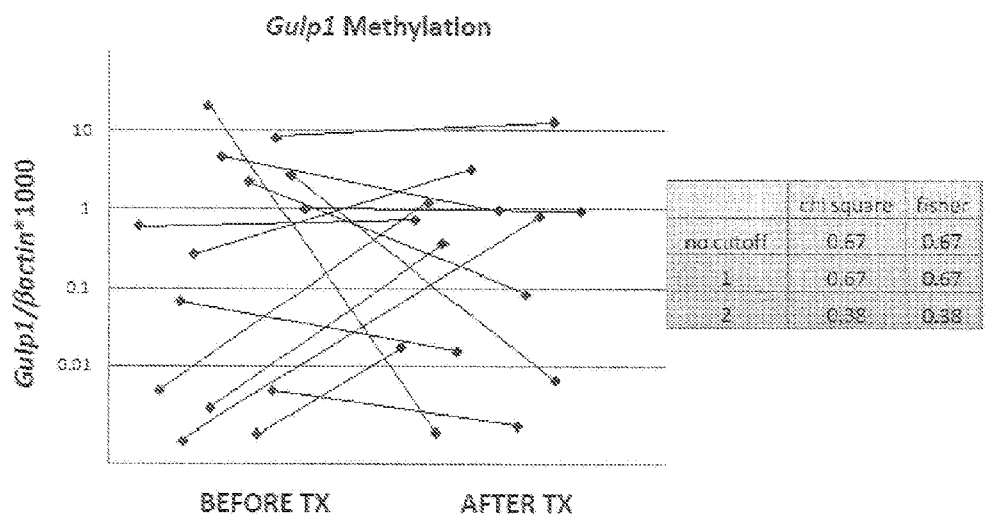
FIG. 20 is a graphical diagram showing promoter methylation levels for the GULP1 gene in the ovarian cancer patient samples divided by before (n=14) and after (n=14) treatment (paired samples are indicated by the connecting lines). The quantity of each methylated gene promoter was expressed as the ratio of the amount of PCR products amplified from the methylated gene to the amount amplified with the reference gene β-actin multiplied by 1,000.
Figure 21:
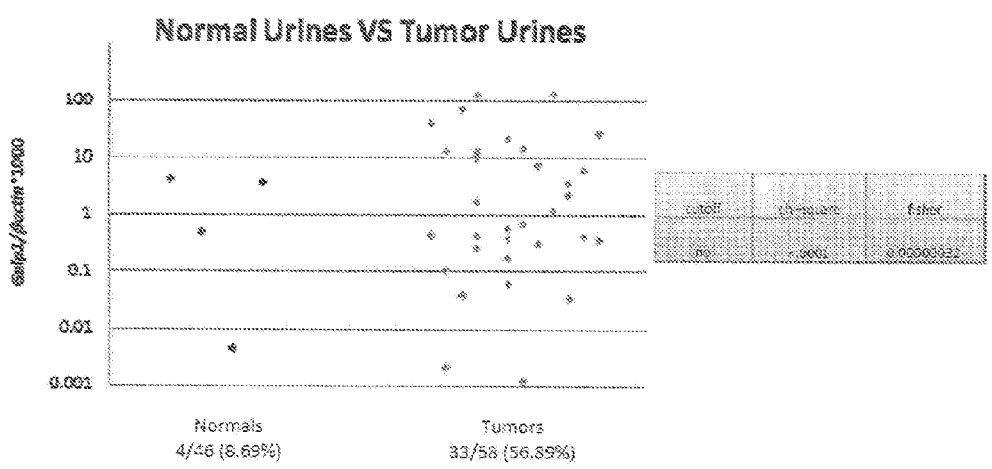
FIG. 21 is a graphical diagram showing promoter methylation levels for the GULP1 gene in the urines from bladder cancer patients (n=58) and normal subjects (n=46). The quantity of each methylated gene promoter was expressed as the ratio of the amount of PCR products amplified from the methylated gene to the amount amplified with the reference gene β-actin multiplied by 1,000.
Figure 22:
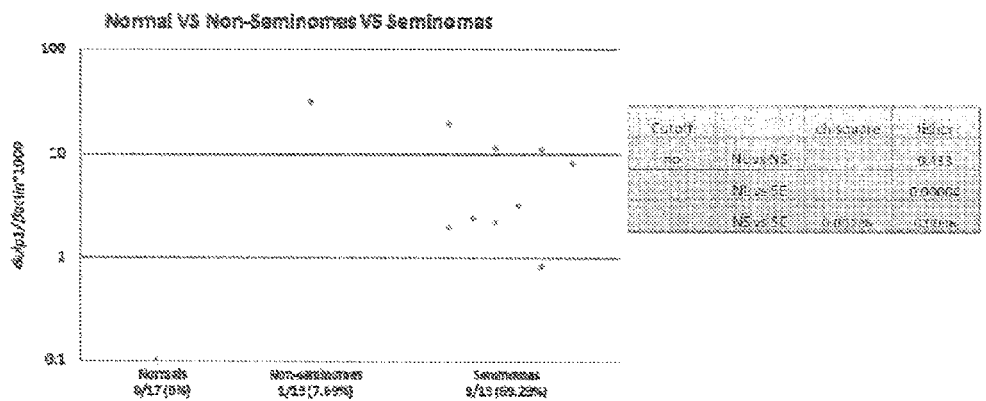
FIG. 22 is a graphical diagram showing promoter methylation levels for the GULP1 gene in the testicular cancer patient samples (Seminomas; n=13, Non-seminomas; n=13), and Normal Testicular Tissues (n=17). The quantity of each methylated gene promoter was expressed as the ratio of the amount of PCR products amplified from the methylated gene to the amount amplified with the reference gene β-actin multiplied by 1,000.
Figure 23:
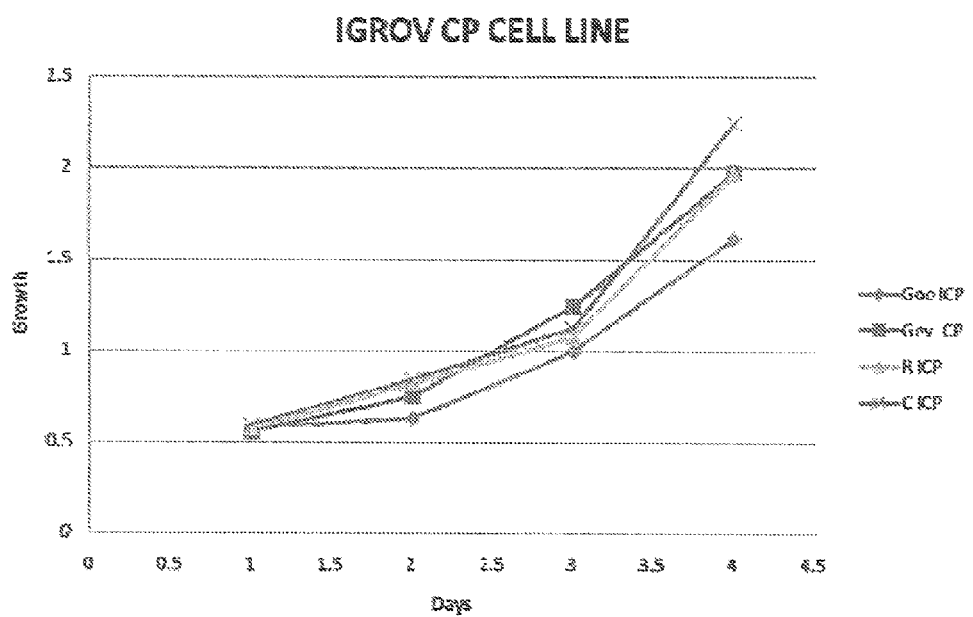
FIG. 23 is a graphical diagram showing analysis of cell growth by a WST-8 Cell Counting Kit-8 (CCK-8 assay). The growth condition of the IGROV CP cells (ovarian cancer cells) were measured after 1, 2, 3 and 4 days. Goe ICP, GULP1 overexpression vector; Gev ICP, control vector; R ICP, only the transfection reagent was added; C ICP, mock/control.
Figure 24:
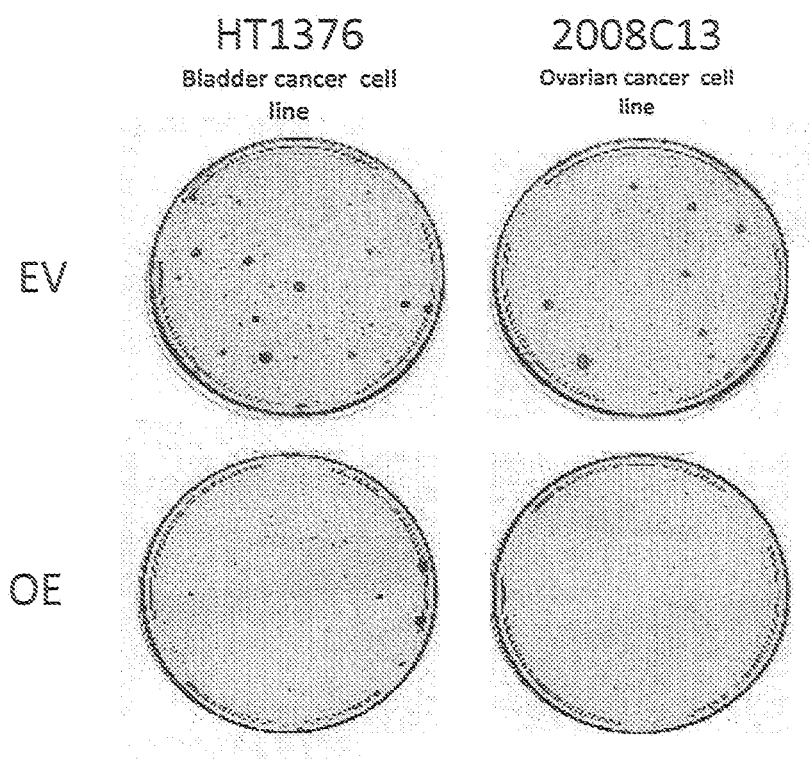
FIG. 24 is a pictorial diagram showing that ectopic expression of GULP1 inhibits tumor cell growth. The effect of ectopic expression of GULP1 on carcinoma cell clonogenicity was investigated by colony formation assay. Cells were transfected with GULP1 overexpression vector (OE) or control vector (EV), and selected with G418. HT 1376=Bladder Cancer Cell Line and 2008 C13=Ovarian Cancer Cell Line.

The present invention is based on the discovery that several genes have promoters that are hypermethylated, thus typically resulting in transcriptional down-regulation in cancer. Accordingly, in a first embodiment of the invention, there are provided methods for identifying a cell that exhibits or is predisposed to exhibiting unregulated growth. The method includes determining the methylation state of a gene or a regulatory region in at least one gene in the cell, wherein the at least one gene is hypermethylated as compared to a corresponding normal cell not exhibiting unregulated growth, thereby identifying the cell as exhibiting or predisposed to exhibiting unregulated growth.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

It has been shown that genetic changes, which include deletions, amplifications, and mutations in DNA sequence, and epigenetic changes, which refer to heritable changes in the gene expression that occur without changes to the DNA sequence, contribute to the development and progression of tumor cells.

The genes or regulatory regions thereof whose methylation status is detected in the methods provided herein can be any gene or regulatory region thereof identified as hypermethylated in a cell exhibiting unregulated growth as compared to a corresponding normal cell, not undergoing unregulated cell growth. In certain embodiments, at least two genes or regulatory regions are hypermethylated and the at least two genes are coordinately expressed in the cell undergoing unregulated cell growth. In other aspects, at least three, or at least four, or at least five, or more genes or regulatory regions are hypermethylated.

As used herein, the term "hypermethylated" refers to the addition of one or more methyl groups to a cytosine ring in a DNA sequence to form methyl cytosine as compared to a "normal" gene. Such methylations typically only occur on cytosines that precede a guanosine in the DNA sequence, which is commonly known as a CpG dinucleotide. There are CpG-rich regions known as CpG islands which span the 5' end region (e.g., promoter, untranslated region and exon 1) of many genes and are usually unmethylated in normal cells. The methylation patterns of cancer cells are altered as compared to the corresponding normal cells, undergoing global DNA hypomethylation as well as hypermethylation of CpG islands. Hypomethylation has been hypothesized to contribute to oncogenesis by transcriptional activation of oncogenes and latent transposons, or by chromosome instability. Aberrant promoter hypermethylation and histone modification, leading to transcriptional inactivation and gene silencing, is a common phenomenon in human cancer cells and likely one of the earliest events in carcinogenesis. As such, hypermethylation of CpG islands in gene promoter regions is a frequent mechanism of inactivation of tumor suppressor genes.

As used herein "corresponding normal cells" means cells that are from the same organ and of the same type as the cells being examined, but are known to be free from the disorder being diagnosed or treated. In one aspect, the corresponding normal cells comprise a sample of cells obtained from a healthy individual. Such corresponding normal cells can, but need not be, from an individual that is age-matched to the individual providing the cells being examined. In another aspect, the corresponding normal cells comprise a sample of cells obtained from an otherwise healthy portion of tissue of a subject having ovarian cancer.

Accordingly, the present invention is designed to profile methylation alterations on promoter regions of selected genes in ovarian tumors with the aim of identifying candidate markers for diagnosis and prognosis of the disease, with sensitivity and specificity necessary to identify subjects with early asymptomatic ovarian cancer, as well as disease monitoring, therapeutic prediction and new targets for therapy.

In one embodiment, the gene or regulatory region is two or more genes including those listed here and/or additional genes (the "target genes"). Exemplary target genes include, but are not limited to, at least one gene or regulatory region thereof selected from GULP1, CSGALNACT2, PGP9.5, HIC1, AIM1, APC, PAK3, MCAM, MGMT, KIF1A; CCNA1, ESR1, SSBP2, GSTP1, FKBP4, VGF, and any combination thereof. In some embodiments, the gene or regulatory region thereof is one or more of GULP1, CSGALNACT2, PGP9.5, HIC1, AIM1, APC, PAK3, MCAM, MGMT, KIF1A, CCNA1, ESR1, SSBP2, GSTP1, FKBP4, VGF, and any combination thereof.

As provided herein, hypermethylation may occur in the gene or regulatory region thereof. In some embodiments, the hypermethylation occurs within the regulatory region of the genes identified herein, in particular embodiments, the hypermethylation is in the promoter sequence of the regulatory region. For example, the hypermethylation may be in a CpG dinucleotide motif of the promoter. As such, in one embodiment, the methylation status of the regulatory regions of one or more of GULP1, CSGALNACT2, PGP9.5, HIC1, AIM1, APC, PAK3, MCAM, MGMT, KIF1A, CCNA1, ESR1, SSBP2, GSTP1, FKBP4, and VGF, is determined. It is understood that this list is not meant to be limiting but instead, illustrative.

Thus, in one aspect, the invention provides a method for diagnosing ovarian cancer in a subject having or at risk of developing ovarian cancer. The method includes determining the methylation state of a gene or a regulatory region of a gene in at least two genes wherein at least one gene is selected from the group consisting of GULP1, CSGALNACT2, PGP9.5, HIC1, AIM1, APC, PAK3, MCAM, MGMT, KIF1A, CCNA1, ESR1, SSBP2, GSTP1, FKBP4, VGF, and any combination thereof, in a nucleic acid sample from the subject, wherein the methylation state is hypermethylated as compared to a corresponding normal cell, and wherein hypermethylation is indicative of a subject having or at risk of developing ovarian cancer. In another embodiment, the method includes contacting a nucleic acid-containing sample from cells of the subject with an agent that provides a determination of the methylation state of at least one gene or a regulatory region of a gene, wherein the at least one regulatory region is hypermethylated in a cell undergoing unregulated cell growth as compared to a corresponding normal cell; and identifying hypermethylation of the regulatory region in the nucleic acid-containing sample, as compared to the same region of the at least one regulatory region in a subject not having the proliferative disorder, wherein hypermethylation is indicative of a subject having or at risk of developing ovarian cancer.

As used herein, the term "cell proliferative disorder" refers to malignant as well as non-malignant cell populations which often differ from the surrounding tissue both morphologically and genotypically. In some embodiments, the cell proliferative disorder is a cancer. In particular embodiments the cancer may be a carcinoma or a sarcoma. A cancer can include, but is not limited to, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, testicular cancer, bladder cancer, cervical cancer, and adenomas. In one embodiment, the cancer is ovarian cancer.

The nucleic acid-containing sample for use in the invention methods may be virtually any biological sample that contains nucleic acids from the subject. The biological sample can be a tissue sample which contains 1 to 10,000,000, 1000 to 10,000,000, or 1,000,000 to 10,000,000 somatic cells. However, it is possible to obtain samples that contain smaller numbers of cells, even a single cell in embodiments that utilize an amplification protocol such as PCR. The sample need not contain any intact cells, so long as it contains sufficient material (e.g., protein or genetic material, such as RNA or DNA) to assess methylation status or gene expression levels.

As used herein, the terms "sample" and "biological sample" refer to any sample suitable for the methods provided by the present invention. A sample of cells used in the present method can be obtained from tissue samples or bodily fluid from a subject, or tissue obtained by a biopsy procedure (e.g., a needle biopsy) or a surgical procedure. In one embodiment, the biological or tissue sample can be drawn from any tissue that is susceptible to cancer. Thus, exemplary samples include, but are not limited to, a tissue sample, a frozen tissue sample, a biopsy specimen, a surgical specimen, a cytological specimen, whole blood, bone marrow, cerebral spinal fluid, peritoneal fluid, pleural fluid, lymph fluid, serum, mucus, plasma, urine, chyle, stool, sputum, nipple aspirate and saliva. In certain embodiments, the sample can be a fraction of a blood sample such as a peripheral blood lymphocyte (PBL) fraction. Methods for isolating PBLs from whole blood are well known in the art. In addition, it is possible to use a blood sample and enrich the small amount of circulating cells from a tissue of interest, e.g., ovaries, breast, etc., using methods known in the art.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. In addition, the term "subject" may refer to a culture of cells, where the methods of the invention are performed in vitro to assess, for example, efficacy of a therapeutic agent.

Numerous methods for analyzing methylation status of a gene or regulatory region are known in the art and can be used in the methods of the present invention to identify hypermethylation. As illustrated in the Examples herein, analysis of methylation can be performed by bisulfite genomic sequencing.

Bisulfite ions, for example, sodium bisulfite, convert non-methylated cytosine residues to bisulfite modified cytosine residues. The bisulfite ion treated gene sequence can be exposed to alkaline conditions, which convert bisulfite modified cytosine residues to uracil residues. Sodium bisulfite reacts readily with the 5,6-double bond of cytosine (but poorly with methylated cytosine) to form a sulfonated cytosine reaction intermediate that is susceptible to deamination, giving rise to a sulfonated uracil. The sulfonate group can be removed by exposure to alkaline conditions, resulting in the formation of uracil. The DNA can be amplified, for example, by PCR, and sequenced to determine whether CpG sites are methylated in the DNA of the sample. Uracil is recognized as a thymine by Taq polymerase and, upon PCR, the resultant product contains cytosine only at the position where 5-methylcytosine was present in the starting template DNA. One can compare the amount or distribution of uracil residues in the bisulfite ion treated gene sequence of the test cell with a similarly treated corresponding non-methylated gene sequence. A decrease in the amount or distribution of uracil residues in the gene from the test cell indicates methylation of cytosine residues in CpG dinucleotides in the gene of the test cell. The amount or distribution of uracil residues also can be detected by contacting the bisulfite ion treated target gene sequence, following exposure to alkaline conditions, with an oligonucleotide that selectively hybridizes to a nucleotide sequence of the target gene that either contains uracil residues or that lacks uracil residues, but not both, and detecting selective hybridization (or the absence thereof) of the oligonucleotide.

In another embodiment, the gene is contacted with hydrazine, which modifies cytosine residues, but not methylated cytosine residues, then the hydrazine treated gene sequence is contacted with a reagent such as piperidine, which cleaves the nucleic acid molecule at hydrazine modified cytosine residues, thereby generating a product comprising fragments. By separating the fragments according to molecular weight, using, for example, an electrophoretic, chromatographic, or mass spectrographic method, and comparing the separation pattern with that of a similarly treated corresponding non-methylated gene sequence, gaps are apparent at positions in the test gene contained methylated cytosine residues. As such, the presence of gaps is indicative of methylation of a cytosine residue in the CpG dinucleotide in the target gene of the test cell.

Modified products can be detected directly, or after a further reaction that creates products that are easily distinguishable. Means which detect altered size and/or charge can be used to detect modified products, including but not limited to electrophoresis, chromatography, and mass spectrometry. Examples of such chemical reagents for selective modification include hydrazine and bisulfite ions. Hydrazine-modified DNA can be treated with piperidine to cleave it. Bisulfite ion-treated DNA can be treated with alkali. Other means which are reliant on specific sequences can be used, including but not limited to hybridization, amplification, sequencing, and ligase chain reaction. Combinations of such techniques can be used as is desired.

In another example, methylation status may be assessed using, real-time methylation specific PCR (QMSP). For example, the methylation level of the promoter region of one or more of the target genes can be determined by determining the amplification level of the promoter region of the target gene based on amplification-mediated displacement of one or more probes whose binding sites are located within the amplicon. In general, real-time quantitative methylation specific PCR is based on the continuous monitoring of a progressive fluorogenic PCR by an optical system. Such PCR systems are well-known in the art and usually use two amplification primers and an additional amplicon-specific, fluorogenic hybridization probe that specifically binds to a site within the amplicon. The probe can include one or more fluorescence labeled moieties. For example, the probe can be labeled with two fluorescent dyes: 1) a 6-carboxy-fluorescein (FAM), located at the 5'-end, which serves as reporter, and 2) a 6-carboxy-tetramethyl-rhodamine (TAMRA), located at the 3'-end, which serves as a quencher. When amplification occurs, the 5'-3' exonuclease activity of the Taq DNA polymerase cleaves the reporter from the probe during the extension phase, thus releasing it from the quencher. The resulting increase in fluorescence emission of the reporter dye is monitored during the PCR process and represents the number of DNA fragments generated.

In other embodiments, hypermethylation can be identified through nucleic acid sequencing after bisulfite treatment to determine whether a uracil or a cytosine is present at a specific location within a gene or regulatory region. If uracil is present after bisulfite treatment, then the nucleotide was unmethylated. Hypermethylation is present when there is a measurable increase in methylation.

In another embodiment, the method for analyzing methylation of the target gene can include amplification using a primer pair specific for methylated residues within the target gene. Thus, selective hybridization or binding of at least one of the primers is dependent on the methylation state of the target DNA sequence (Herman et al., *Proc. Natl. Acari Sci. USA*, 93:9821 (1996)). For example, the amplification reaction can be preceded by bisulfite treatment, and the primers can selectively hybridize to target sequences in a manner that is dependent on bisulfite treatment. As such, one primer can selectively bind to a target sequence only when one or more bases of the target sequence is altered by bisulfite treatment, thereby being specific for a methylated target sequence.

Other methods are known in the art for determining methylation status of a target gene, including, but not limited to, array-based methylation analysis (see Gitan et al., *Genome Res* 12:158-64, 2002) and Southern blot analysis.

Methods using an amplification reaction can utilize a real-time detection amplification procedure. For example, the method can utilize molecular beacon technology (Tyagi S., et al., *Nature Biotechnology*, 14: 303 (1996)) or TAQMAN™ technology (Holland, P. M., et al., *Proc. Natl. Acad. Sci. USA*, 88:7276 (1991)).

In addition, methyl light (Trinh, et al. DNA methylation analysis by MethyLight technology, Methods, 25(4):456-62 (2001), incorporated herein in its entirety by reference), Methyl Heavy (Epigenomics, Berlin, Germany), or SNuPE (single nucleotide primer extension) (See e.g., Watson, et al., *Genet Res*. 75(3):269-74 (2000)) can be used in the methods of the present invention related to identifying altered methylation of the genes or regulatory regions provided herein. Additionally, methyl light, methyl heavy, and array-based methylation analysis can be performed, by using bisulfite treated DNA that is then PCR-amplified, against microarrays of oligonucleotide target sequences with the various forms corresponding to unmethylated and methylated DNA.

The degree of methylation in the DNA associated with the gene or genes or regulatory regions thereof, may be measured by fluorescent in situ hybridization (FISH) by means of probes that identify and differentiate between genomic DNAs, which exhibit different degrees of DNA methylation. FISH is described in Human chromosomes: principles and techniques (Editors, Ram S. Verma, Arvind Babu Verma, Ram S.) 2nd ed., New York: McGraw-Hill, 1995, and de Capoa A., Di Leandro M., Grappelli C., Menendez F., Poggesi I., Gianotti P., Marotta, M. R., Spano A., Rocchi M., Archidiacono N., Niveleau A. Computer-assisted analysis of methylation status of individual interphase nuclei in human cultured cells. *Cytometry*. 31:85-92, 1998, which is incorporated herein by reference. In this case, the biological sample will typically be any that contains sufficient whole cells or nuclei to perform short term culture. Usually, the sample will be a tissue sample that contains 10 to 10,000, or, for example, 100 to 10,000, whole somatic cells. However, as indicated above, in one embodiment, the biological sample can be a tissue sample which contains 1 to 10,000,000, 1000 to 10,000,000, or 1,000,000 to 10,000,000 somatic cells.

In another embodiment, methylation-sensitive restriction endonucleases can be used to detect methylated CpG dinucleotide motifs. Such endonucleases may either preferentially cleave methylated recognition sites relative to non-methylated recognition sites or preferentially cleave non-methylated relative to methylated recognition sites. Examples of the former are Acc III, Ban I, BstN I, Msp I, and Xma I. Examples of the latter are Acc II Ava I, BssH II, BstU I, Hpa II, and Not I. Alternatively, chemical reagents can be used that selectively modify either the methylated or non-methylated form of CpG dinucleotide motifs.

In some embodiments, hypermethylation of the target gene is detected by detecting decreased expression of the that gene. Expression of a gene can be assessed using any means known in the art. Typically expression is assessed and compared in test samples and control samples which may be normal, non-malignant cells. The test samples may contain cancer cells or pre-cancer cells or nucleic acids from the cells. Methods employing hybridization to nucleic acid probes can be employed for measuring specific mRNAs. Such methods include using nucleic acid probe arrays (microarray technology), in situ hybridization, and using Northern blots. Messenger RNA can also be assessed using amplification techniques, such as RT-PCR. Advances in genomic technologies now permit the simultaneous analysis of thousands of genes, although many are based on the same concept of specific probe-target hybridization. Sequencing-based methods are an alternative; these methods started with the use of expressed sequence tags (ESTs), and now include methods based on short tags, such as serial analysis of gene expression (SAGE) and massively parallel signature sequencing (MPSS). Differential display techniques provide yet another means of analyzing gene expression; this family of techniques is based on random amplification of cDNA fragments generated by restriction digestion, and bands that differ between two tissues identify cDNAs of interest. Moreover, specific proteins can be assessed using any convenient method including, but not limited to, immunoassays and immuno-cytochemistry. Most such methods will employ antibodies that are specific for the particular protein or protein fragments. The sequences of the mRNA (cDNA) and proteins of the target genes of the present invention are known in the art and publicly available.

As used herein, the term "selective hybridization" or "selectively hybridize" refers to hybridization under moderately stringent or highly stringent physiological conditions, which can distinguish related nucleotide sequences from unrelated nucleotide sequences.

As known in the art, in nucleic acid hybridization reactions, the conditions used to achieve a particular level of stringency will vary, depending on the nature of the nucleic acids being hybridized. For example, the length, degree of complementarity, nucleotide sequence composition (for example, relative GC:AT content), and nucleic acid type, i.e., whether the oligonucleotide or the target nucleic acid sequence is DNA or RNA, can be considered in selecting hybridization conditions. An additional consideration is whether one of the nucleic acids is immobilized, for example, on a filter. Methods for selecting appropriate stringency conditions can be determined empirically or estimated using various formulas, and are well known in the art (see, for example, Sambrook et al., supra, 1989).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, for example, high stringency conditions, or each of the conditions can be used, for example, for 10 to 15 minutes each, in the order listed above, repeating any or all of the steps listed.

The term "nucleic acid molecule" is used broadly herein to mean a sequence of deoxyribonucleotides or ribonucleotides that are linked together by a phosphodiester bond. As such, the term "nucleic acid molecule" is meant to include DNA and RNA, which can be single stranded or double stranded, as well as DNA/RNA hybrids. Furthermore, the term "nucleic acid molecule" as used herein includes naturally occurring nucleic acid molecules, which can be isolated from a cell, for example, a particular gene of interest, as well as synthetic molecules, which can be prepared, for example, by methods of chemical synthesis or by enzymatic methods such as by the polymerase chain reaction (PCR), and, in various embodiments, can contain nucleotide analogs or a backbone bond other than a phosphodiester bond.

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Of course, it will be recognized that an "oligonucleotide" also can encode a peptide. As such, the different terms are used primarily for convenience of discussion.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

In yet another aspect, the invention provides methods of determining the prognosis of a subject having ovarian cancer. The method includes determining the methylation state of a gene or a regulatory region of a gene in at least two genes in a nucleic acid sample from the subject. A comparison of the hypermethylation of the gene or regulatory region thereof, as compared to that of a corresponding normal cell in the subject or a subject not having the disorder, is indicative of a poor prognosis.

In another aspect, the invention provides methods of identifying a cell that exhibits or is predisposed to exhibiting unregulated growth. The method includes detecting hypermethylation of a gene or regulatory region of a gene in at least two genes wherein at least one gene is selected from the group consisting of GULP1, CSGALNACT2, PGP9.5, HIC1, AIM1, APC, PAK3, MCAM, MGMT, KIF1A, CCNA1, ESR1, SSBP2, GSTP1, FKBP4, VGF, and any combination thereof. Hypermethylation of at least one gene, as compared to a corresponding normal cell not exhibiting unregulated growth, identifies the cell as exhibiting or predisposed to exhibiting unregulated growth.

In another aspect, the invention provides methods of ameliorating symptoms associated with ovarian cancer in a subject in need thereof. The method includes administering to the subject an agent that demethylates at least one gene or regulatory region in a gene that is hypermethylated as compared to that of a subject not having the disorder, thereby reducing expression of the at least one gene and ameliorating the symptoms associated with ovarian cancer. The signs or symptoms to be monitored will be characteristic of ovarian cancer and will be well known to the skilled clinician, as will the methods for monitoring the signs and conditions.

As used herein, the terms "administration" or "administering" are defined to include the act of providing a compound or pharmaceutical composition of the invention to a subject in need of treatment. Exemplary forms of administration include, but are not limited to, topical administration, and injections such as, without limitation, intravitreal, intravenous, intramuscular, intra-arterial, intra-thecal, intra-capsular, intra-orbital, intra-cardiac, intra-dermal, intra-peritoneal, trans-tracheal, sub-cutaneous, sub-cuticular, intra-articulare, sub-capsular, sub-arachnoid, intra-spinal and intra-sternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

The total amount of a compound or composition to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the compound or composition to treat ovarian cancer and/or ameliorate the symptoms associated therewith in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

As used herein, the term "ameliorating" or "treating" means that the clinical signs and/or the symptoms associated with cellular proliferative disorder (e.g., ovarian cancer) are lessened as a result of the actions performed. The signs or symptoms to be monitored will be characteristic of the cellular proliferative disorder (e.g., ovarian cancer) and will be well known to the skilled clinician, as will the methods for monitoring the signs and conditions. Also included in the definition of "ameliorating" or "treating" is the lessening of symptoms associated with ovarian cancer in subjects not yet diagnosed as having the specific cancer. As such, the methods may be used as a means for prophylactic therapy for a subject at risk of having ovarian cancer.

As used herein, the term "demethylating agent" is used to refer to any compound that can inhibit methylation, resulting in the expression of the previously hypermethylated silenced genes. Cytidine analogs such as 5-azacytidine (azacitidine) and 5-aza-2-deoxycytidine (decitabine) are the most commonly used demethylating agents. These compounds work by binding to the enzymes that catalyze the methylation reaction, DNA methyltransferases. Thus, in one embodiment, the demethylating agent is 5-azacytidine, 5-aza-2-deoxycytidine, or zebularine. In another embodiment, the demethylating agent is delivered locally to a tumor site or systemically by targeted drug delivery.

Agents that demethylate the hypermethylated gene or regulatory region of the gene can be contacted with cells in vitro or in vivo for the purpose of restoring normal gene expression to the cell. Efficacy of the treatment can be assessed by detecting decreased expression or demethylation of a gene selected from the group consisting of GULP1, CSGALNACT2, PGP9.5, HIC1, AIM1, APC, PAK3, MCAM, MGMT, KIF1A, CCNA1, ESR1, SSBP2, GSTP1, FKBP4, and VGF.

Once disease is established and a treatment protocol is initiated, the methods of the invention may be repeated on a regular basis to evaluate whether the methylation state of a gene or regulatory region thereof, in the subject begins to approximate that which is observed in a normal subject. Alternatively, or in addition thereto, the methods of the invention may be repeated on a regular basis to evaluate whether the symptoms associated with ovarian cancer have been decreased or ameliorated. The results obtained from successive assays may be used to show the efficacy of treatment over a period ranging from several days to months to years. Accordingly, the invention is also directed to methods for determining whether a subject is responsive to a particular therapeutic regimen. The methods include determining the methylation state of one or more genes or regulatory regions thereof, selected from the group consisting of GULP1, CSGALNACT2, PGP9.5, HIC1, AIM1, APC, PAK3, MCAM, MGMT, KIF1A, CCNA1, ESR1, SSBP2, GSTP1, FKBP4, and VGF. A comparison of the hypermethylation of the gene or regulatory region thereof, as compared to that of a corresponding normal cell in the subject or a subject not having the disorder is indicative of a subject who is responsive to the therapeutic regimen.

In one embodiment, the therapeutic regimen is administration of one or more chemotherapeutic agent. In another embodiment, the therapeutic regimen is administration of one or more chemotherapeutic agents in combination with one or more demethylating agents.

Exemplary chemotherapeutic agents include, but are not limited to, antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecolcine, etoposide, taxane, anthracycline antibiotic, doxorubicin, daunorubicin, caminomycin, epirubicin, idarubicin, mitoxanthrone, 4-dimethoxy-daunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methotrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-α, etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis. Thus, in one embodiment, the therapeutic regimen is a administration of cisplatin in combination with paclitaxel.

The materials for use in the methods of the invention are ideally suited for the preparation of a kit. As such, in another aspect, the invention provides a kit for detection of a methylated CpG-containing nucleic acid in determining the methylation status of one or more genes or regulatory regions thereof. Such a kit may comprise a carrier device containing one or more containers such as vials, tubes, and the like, each of the containers comprising one of the separate elements to be used in the method. The kit may contain reagents, as described above for differentially modifying methylated and non-methylated cytosine residues. One of the containers may include a probe which is or can be delectably labeled. Such probe may be a nucleic acid sequence specific for a promoter region associated with a gene selected from the group consisting of GULP1, CSGALNACT2, PGP9.5, HIC1, AIM1, APC, PAK3, MCAM, MGMT, KIF1A, CCNA1, ESR1, SSBP2, GSTP1, FKBP4, and VGF. For example, oligonucleotide probes of the invention can be included in a kit and used for detecting the presence of hypermethylated nucleic acid sequences in a sample containing a nucleic acid sequence of the genes GULP1, CSGALNACT2, PGP9.5, HIC1, AIM1, APC, PAK3, MCAM, MGMT, KIF1A, CCNA1, ESR1, SSBP2, GSTP1, FKBP4, and VGF. The kit may also include a container comprising a reporter, such as an enzymatic, fluorescent, or radionucleotide label to identify the detectably labeled oligonucleotide probe.

In certain embodiments, the kit utilizes nucleic acid amplification in detecting the target nucleic acid. In such embodiments, the kit will typically contain both a forward and a reverse primer for each target gene. Such oligonucleotide primers are based upon identification of the flanking regions contiguous with the target nucleotide sequence. Accordingly, the kit may contain primers useful to amplify and screen a promoter region of a gene selected from the group consisting of GULP1, CSGALNACT2, PGP9.5, HIC1, AIM1, APC, PAK3, MCAM, MGMT, KIF1A, CCNA1, ESR1, SSBP2, GSTP1, FKBP4, and VGF. If there is a sufficient region of complementarity, e.g., 12, 15, 18, or 20 nucleotides, then the primer may also contain additional nucleotide residues that do not interfere with hybridization but may be useful for other manipulations. For example, such other residues may be sites for restriction endonuclease cleavage, for ligand binding or for factor binding or linkers or repeats. The oligonucleotide primers may or may not be such that they are specific for modified methylated residues. The kit may optionally contain oligonucleotide probes. The probes may be specific for sequences containing modified methylated residues or for sequences containing non-methylated residues. The kit may optionally contain reagents for modifying methylated cytosine residues. The kit may also contain components for performing amplification, such as a DNA polymerase and deoxyribonucleotides. Means of detection may also be provided in the kit, including detectable labels on primers or probes. Kits may also contain reagents for detecting gene expression for one of the markers of the present invention. Such reagents may include probes, primers, or antibodies, for example. In the case of enzymes or ligands, substrates or binding partners may be used to assess the presence of the marker. In particular embodiments, the kit may include one or more primers or primer pairs selected from the sequences set forth in SEQ ID NOs: 1-51.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLE 1

This example illustrates the comprehensive approach for identification of ovarian cancer specific methylation markers.

Fourteen genes already known to be inactivated by promoter methylation in various cancers were evaluated in ovary tumors and normal samples by quantitative fluorogenic real-time methylation specific PCR (QMSP). The selected genes were: GULP1, CSGALNACT2, PGP9.5, HIC1, AIM1, APC, PAK3, MCAM, MGMT, KIF1A, CCNA1, ESR1, SSBP2, GSTP1, FKBP4, and VGF.

An evaluation set consisting of 33 ovarian tumor samples and three normal ovarian cell lines were first tested (see Table 1). Based on sensitivity and specificity, five genes (PGP9.5, HIC1, MCAM, ESR1, and VGF) were selected for further analysis in an independent test set of 24 samples (see Tables 2 and 3). In this set of samples, MCAM and HIC1 methylation was observed in 96% (23/24) and 75% of the (18/24) samples, respectively. ESR1 and PGP9.5 promoter methylation was found in 42% (10/24) samples, and 33% (8/24) of the tumor samples, respectively. The high frequencies of hypermethylation found by QMSP for these five genes in two independent sets of tumor samples suggest that these epigenetic alterations are important in ovarian cancer development.

TABLE 1

Demographic and clinical characteristics of ovarian cancer patients

| characteristics | No. (%) patients | |
|---|---|---|
| | Evaluation set | Independent test set |
| Age | | |
| Median (range) | 57 (23-79) | 56 (37-77) |
| ≥60 | 13 (39) | 9 (38) |
| <60 | 20 (61) | 15 (62) |
| Race | | |
| Caucasian | 24 (73) | 24 (100) |
| African-american | 8 (24) | 0 (0) |

TABLE 1-continued

Demographic and clinical characteristics of ovarian cancer patients

| characteristics | No. (%) patients Evaluation set | No. (%) patients Independent test set |
|---|---|---|
| Unknown | 1 (3) | 0 (0) |
| Stage |  |  |
| Early |  |  |
| I | 15 (46) | 6 (25) |
| II | 1 (3) | 4 (17) |
| Advanced |  |  |
| III | 14 (42) | 12 (50) |
| IV | 3 (9) | 1 (4) |
| Unknown | 0 (0) | 1 (4) |
| Grade |  |  |
| Borderline | 12 (36) | 0 (0) |
| GX | 0 (0) | 1 (4) |
| G1 | 0 (0) | 2 (8) |
| G2 | 8 (24) | 5 (21) |
| G3 | 13 (40) | 12 (50) |
| Unknown | 0 (0) | 4 (17) |
| Tumor type |  |  |
| EOC | 33 (100) | 18 (75) |
| Germ cell | 0 (0) | 1 (4) |
| Stromal | 0 (0) | 0 (0) |
| Secondary (mets.) | 0 (0) | 4 (17) |
| Unknown | 0 (0) | 1 (4) |
| EOC Histology |  |  |
| Serous-papillary | 33 (100) | 11 (46) |
| Endometrioid | 0 (0) | 4 (17) |
| Mucinous | 0 (0) | 2 (8) |
| Squamous | 0 (0) | 0 (0) |
| Undifferentiated | 0 (0) | 1 (4) |
| Unknown | 0 (0) | 6 (25) |
| Chemotherapy Response |  |  |
| Yes | 0 (0) | 13 (54) |
| No | 0 (0) | 10 (42) |
| Unknown | 33 (100) | 1 (4) |
| Smoking status |  |  |
| Non-smoker | 16 (48) | 19 (79) |
| Smoker | 2 (6) | 5 (21) |
| Unknown | 15 (46) | 0 (0) |
| Alcohol consumption |  |  |
| Current | 6 (48) | 2 (8) |
| No | 12 (6) | 22 (92) |
| Unknown | 15 (46) | 0 (0) |
| Chemotherapy |  |  |
| Yes | 11 (33) | 23 (96) |
| No | 9 (27) | 1 (4) |
| Unknown | 13 (40) | 0 (0) |
| Recurrence |  |  |
| Yes | 4 (12) | 14 (58) |
| No | 0 (0) | 10 (42) |
| Unknown | 29 (88) | 0 (0) |
| Metastasis |  |  |
| Yes | 1 (3) | 0 (0) |
| No | 32 (97) | 0 (0) |
| Unknown | 0 (0) | 24 (100) |
| Deaths |  |  |
| Yes | 9 (27) | 11 (46) |
| No | 24 (73) | 13 (54) |
| Unknown | 0 (0) | 0 (0) |
| Total | 33 (100) | 24 (100) |

An established pharmacologic unmasking strategy that they performed using three human ovarian cancer cell lines and three normal ovarian cell lines. Computational analysis was then used to identify cancer-specific methylated genes. 43 highly-ranked genes were tested, ten novel genes (DKK1, CSGALNACT2, CAV1, CLIP4, TFGB2, GATA6iI, BAMBI, DNAJC6, NT5E, and GULP1) were identified as potential cancer-specific methylated genes.

TABLE 2

Promoter methylation frequency for 14 genes analyzed in the evaluation set of samples and 5 genes in the independent test set

| | Evaluation Set Methylation Positive % | | | Independent Set Methylation Positive % | | | | Sensitivity | Specificity |
|---|---|---|---|---|---|---|---|---|---|
| Gene | Tumor | Controls | P[1] | Tumor | Controls | P[1] | P[2] | (%) | (%) |
| ESR1 | 30 (10/33) | 0 (0/9) | 0.086 | 42 (10/24) | 50 (3/6) | 1 | 0.367 | 35 | 75 |
| MCAM | 45 (15/33) | 0 (0/9) | 0.016 | 96 (23/24) | 50 (3/3) | 0.018 | 0.002 | 66.7 | 75 |
| HIC1 | 67 (22/33) | 0 (0/9) | <0.0001 | 75 (18/24) | 33 (2/6) | 0.061 | 0.0004 | 70.2 | 83.3 |
| PGP9.5 | 21 (7/33) | 0 (0/9) | 0.314 | 33 (8/24) | 0 (0/6) | 0.155 | 0.031 | 26.3 | 100 |
| VGF | 24 (8/33) | 0 (0/9) | 0.118 | 54 (13/24) | 0 (0/6) | 0.024 | 0.016 | 36.8 | 100 |
| CCNA1 | 3 (1/33) | 0 (0/9) | ND[3] | ND | | | | | |
| PAK3 | 18 (6/33) | 100 (9/9) | ND | ND | | | | | |
| SSBP2 | 9 (3/33) | 11 (1/8) | ND | ND | | | | | |
| APC | 15 (5/33) | 0 (0/9) | 0.567 | ND | | | | | |
| FKBP4 | 9 (3/33) | 0 (0/9) | 0.577 | ND | | | | | |
| GSTP1 | 0 (0/33) | 0 (0/9) | ND | ND | | | | | |
| KIF1A | 6 (2/33) | 11 (1/9) | ND | ND | | | | | |
| MGMT | 3 (1/33) | 0 (0/9) | ND | ND | | | | | |
| AIM1 | 3 (1/33) | 0 (0/9) | ND | ND | | | | | |

[1]Fisher's exact test (two sided);
[2]Fisher's exact test (two sided) for combined group (evaluation and independent);
[3]ND = Not analyzed

TABLE 3

Spearman correlation matrix of promoter methylation
of 5 genes in ovarian tumor samples

| Genes  | ESR1 | MCAM  | HIC1  | PGP9.5 | VGF  |
|--------|------|-------|-------|--------|------|
| ESR1   | 1.00 |       |       |        |      |
| MCAM   | 0.24 | 1.00  |       |        |      |
| HIC1   | 0.30 | 0.67* | 1.00  |        |      |
| PGP9.5 | 0.23 | 0.30  | 0.09  | 1.00   |      |
| VGF    | 0.23 | 0.48* | 0.47* | 0.31   | 1.00 |

EXAMPLE 2

This example is intended to identify ovarian cancer methylation specific patterns by applying a pharmacologic unmasking method. This approach consists of performing expression microarray on 15 ovarian tumor samples, 10 ovarian surface epithelium brushing (normal ovary), 3 ovarian cancer derived cell lines (A2780, 2008, IGROV) and 3 normal cell lines (derived from ovarian inclusion cysts: OSE2A, OSE2B, OSE7). The ovarian cancer cell lines were paired as cisplatin resistant vs. cisplatin sensitive, as follows: 2008C13 vs. 2008; A2780CP vs. A2780; and IGROVCP vs. IGROV. For each cell line, a control (untreated) and a cell treated with 5AZA (re-expression experiment) were also tested. All cells have been treated with a global demethylating agent which will comprehensively uncover genes silenced by promoter hypermethylation. The investigation searched for genes that are differentially expressed between normal cell lines/tissue samples and tumor cell lines/tissue samples, being down-regulated in cancer samples/cell lines when compared to normal, and finally that have been re-activated after the treatment with the demethylating agent.

The microarray platform used was U133 Plus 2.0 from Affymetrix (Santa Clara, Calif.), which contains over 47,000 transcripts. Applying the criteria mentioned above, a list with 250 transcripts (array probes) that corresponded to 88 genes was obtained. Genes having full length transcripts were first selected, which left 79 genes. Any genes without CpG islands in their promoters were then excluded, resulting in a total of 67 genes. Two of these genes have been extensively reported as being hypermethylated in cancer (DAPK and APC), so they were also excluded. Primers for 43 of the 65 genes were then successfully designed to screen the CpG islands contained in the promoter region and determine their methylation status by bisulfite sequencing in 3 tumor cell lines and 3 normal cell lines. Ten candidates where then obtained. And work began with two of them (GULP1 and CSGALNACT2).

EXAMPLE 3

Briefly, cells were split to low density ($1 \times 10^6$ cells/T-75 flask) 24 hours before treatment. Stock solution of 5Aza-dC (Sigma, St. Louis, Mo.) was dissolved in DMSO (Sigma). Cells were treated with 5 μM 5-Aza-deoxycytidine for 5 days. The medium was changed every 24 hours. Baseline expression was established by mock-treated cells with the same volume of DMSO or ethanol.

Oligonucleotide microarray analysis and QRT-PCR analysis. Total cellular RNA was isolated using the RNEASY RNA isolation kit (Qiagen, Valencia, Calif.) according to the manufacturer's instructions. Oligonucleotide microarray analysis was carried out using the GENECHIP U133plus2 Affymetrix expression microarray (Affymetrix, Santa Clara, Calif.). Samples were converted to labeled, fragmented, cRNA per the manufacturer's protocol for use on the expression microarray. Signal intensity and statistical significance were established for each transcript using dChip version 2005. 2-fold increase based on the 90% confidence interval of the result and expression minus baseline>50 was used as the statistical cutoff value after 5Aza-dC to identify silenced candidate genes.

A sorting method, as described below. The U133A microarray platform (Affymetrix, Santa Clara Calif.) has approximately 14,500 probe sets. This resulted in 250 genes deemed significant. The top 88 of these targets were comprehensively evaluated. Presence of CpG islands in these genes was determined by MethPrimer. In order to not exclude genes outside the U133A platform, also considered were all other genes in the U133plus2 platform on the sole basis of 5-aza upfold regulation. 43 genes were studied that had an experimental versus baseline expression (E/B)>2.0, based on the 90% confidence interval and E−B>50. All genes were then studied for the presence of CpG islands in promoters or the first intron. Initially, an in silico approach was used to confirm the presence of a CpG island using the UCSC genome browser which relies on GC content of >50%, >200 bp, >0.6 observed to expected CG's.

DNA extraction. Samples were centrifuged and digested in a solution of detergent (sodium dodecylsulfate) and proteinase K, for removal of proteins bound to the DNA. Samples were first purified and desalted with phenol/chloroform extraction. Digested sample was subjected twice to ethanol precipitation, and subsequently resuspended in 500 μL of LoTE (EDTA 2.5 mmol/L and Tris-HCl 10 mmol/L) and stored at −80° C.

Bisulfite treatment. DNA from the tissue samples was subjected to bisulfite treatment, as described previously (Herman et al., Proc Natl Acad Sci USA 1996; 93:9821-6). In short, 2 μg of genomic DNA was denatured in 0.2 M of NaOH for 30 minutes at 50° C. The denatured DNA was then diluted into 500 μL of a solution of 10 mmol/L hydroquinone and 3 M sodium bisulfite and incubated for 3 hours at 70° C. After incubation, the DNA sample was purified with a SEPHAROSE column (WIZARD DNA Clean-Up System; Promega, Madison, Wis.). Eluted DNA was treated with 0.3 M of NaOH for 10 minutes at room temperature, and precipitated with ethanol. This bisulfite-modified DNA was subsequently resuspended in 120 μL of LoTE (EDTA 2.5 mmol/L and Tris-HCl 10 mmol/L) and stored at −80° C.

Bisulfite sequencing. Bisulfite sequence analysis was performed to check the methylation status in primary tumors and normal tissues, as well as in cell lines (Tables 5A and 5B). Bisulfite-treated DNA was amplified using primers designed using the MethPrimer program (Li and Dahiya, *Bioinformatics* 18(11):1427-31, 2002) to span areas of CpG islands in the promoter or first intron. (see Tables 4A-4C below for primer sequences; ACTB=βactin, which is used as a housekeeping gene to which all methylation values have been normalized). The PCR products were gel-purified using the QIAQUICK gel extraction kit (Qiagen), according to the manufacturer's instructions. Each amplified DNA sample was applied with nested primers to the Applied Biosystems 3700 DNA analyzer using BD terminator dye (Applied Biosystems, Foster City, Calif.).

TABLE 4A

QMSP Forward Primers

| Gene | Forward 5'-3' (primer) | SEQ ID NO: |
|---|---|---|
| ACTB | TGGTGATGGAGGAGGTTTAGTAAGT | 1 |
| AIM1 | CGCGGGTATTGGATGTTAGT | 2 |
| APC | GAACCAAAACGCTCCCCAT | 3 |
| CCNA1 | TCGCGGCGAGTTTATTCG | 4 |
| ESR | GGCGTTCGTTTTGGGATTG | 5 |
| GSTP1 | AGTTGCGCGGCGATTTC | 6 |
| HIC1 | GTTAGGCGGTTAGGGCGTC | 7 |
| KIF1A | GCGCGATAAATTAGTTGGCGATT | 8 |
| MCAM | AGAATTTAGGTCGGTTTTTATCG | 9 |
| MGMT | CGAATATACTAAAACAACCCGCG | 10 |
| PAK3 | TTACGGTCGTCGTTATTATCG | 11 |
| PGP9.5 | CGGCGAGTGAGATTGTAAGGTT | 12 |
| SSBP2 | ATTTTTGCGGTCGTAGCGGT | 13 |
| VGF | GGATAGCGTTCGTAGGCG | 14 |
| FKBP4 | GTTCGTGGTGACGGTCGGTTTCGGG | 15 |
| GULP1 | TGACGTTTGTTATGGTAGCG | 16 |
| CSGALNACT2 | TTAGTTGAGGGTCGTGGTCG | 17 |

TABLE 4B

QMSP Probes

| Gene | Probe 5'-3' (6-FAM-5'-3'-6-TAMRA) | SEQ ID NO: |
|---|---|---|
| ACTB | ACCACCACCCAACACACAATAACAAACACA | 18 |
| AIM1 | GGGAGCGTTGCGGATTATTCGTAG | 19 |
| APC | CCCGTCGAAAACCCGCCGATTA | 20 |
| CCNA1 | CGTTATGGCGATGCGGTTTCGG | 21 |
| ESR | CGATAAAACCGAACGACCCGACGA | 22 |
| GSTP1 | CGGTCGACGTTCGGGGTGTAGCG | 23 |
| HIC1 | CAACATCGTCTACCCAACACACTCTCCTACG | 24 |
| KIF1A | CCTCCCGAAACGCTAATTAACTACGCG | 25 |
| MCAM | ACAATATCAAACCGACGACAACGAC | 26 |
| MGMT | AATCCTCGCGATACGCACCGTTTACG | 27 |
| PAK3 | AACCAAAAAAATAAAAAATCACAACCG | 28 |
| PGP9.5 | TTCGGTCGTATTATTTCGCGTTGCGTAC | 29 |
| SSBP2 | ATATCCAAAACGCCGCGAAACTCC | 30 |
| VGF | GCGCCCAAAAACGACGTAAACCTAAATAC | 31 |

TABLE 4B-continued

QMSP Probes

| Gene | Probe 5'-3' (6-FAM-5'-3'-6-TAMRA) | SEQ ID NO: |
|---|---|---|
| FKBP4 | CAAACTACGAAATAACAATAACGACGC | 32 |
| GULP1 | CGGCGGGGGGTCGGTGAGTA | 33 |
| CSGALNACT2 | CGAACGCTACCTAAACCCCCGAA | 34 |

TABLE 4C

QMSP Reverse Primers

| Gene | Reverse 5'-3' (primer) | SEQ ID NO: |
|---|---|---|
| ACTB | AACCAATAAAACCTACTCCTCCCTTAA | 35 |
| AIM1 | CCGACCCACCTATACGAAAA | 36 |
| APC | TTATATGTCGGTTACGTGCGTTTATAT | 37 |
| CCNA1 | CCGACCGCGACAAACG | 38 |
| ESR | GCCGACACGCGAACTCTAA | 39 |
| GSTP1 | GCCCCAATACTAAATCACGACG | 40 |
| HIC1 | CCGGGCGCCTCCATCGTGT | 41 |
| KIF1A | CTCGACGACTACTCTACGCTAT | 42 |
| MCAM | ACGCAAAATTCTTCTCCCAAAA | 43 |
| MGMT | GTATTTTTTCGGGAGCGAGGC | 44 |
| PAK3 | ACCGAAAATTCTACCCTTCG | 45 |
| PGP9.5 | GAACGATCGCGACCAAATAAATAC | 46 |
| SSBP2 | TTCTACGACAAATCTAACGAA | 47 |
| VGF | AAAAACCGAATTCCCCACCCCG | 48 |
| FKBP4 | ATCCGCTACGCCTACGACG | 49 |
| GULP1 | CGGTGGGAAATCGTGGA | 50 |
| CSGALNACT2 | CGCGTATTTGTTAGACGTGCG | 51 |

TABLE 5

Methylation status of 5 candidate genes in
ovarian cells analyzed by bisulfite sequencing

| CANCER SPECIFIC RELATED GENES | | | | | | | | | |
|---|---|---|---|---|---|---|---|---|---|
| GENE | OSE2A | OSE2B | OSE7 | IGROV | IGROVCP | A2780 | A2780CP | 2008 | 2008C13 |
| T2 | U | U | U | M | M | U | U | U | U |
| C4 | U | M | U | M | M | M | M | U | U |
| B1 | X | X | U | M | M | X | U | M | M |
| G1 | U | U | U | M | M | U | U | M | M |
| NSE | U | U | U | M | M | U | U | U | U |
| DRUG RESPONSE RELATED GENES | | | | | | | | | |
| GENE | OSE2A | OSE2B | OSE7 | IGROV | IGROVCP | A2780 | A2780CP | 2008 | 2008C13 |
| D1 | M | M | X | M | M | M | U | U | M |
| D6 | M | M | U | M | M | U | M | M | M |
| G6 | U | U | U | U | M | U | U | U | U |
| A2 | M | M | U | U/M | M | U | M | M | M |
| C1 | U | U | M | M | U | M | U | U | U |

U Unmethylated
M Methylated
X No result

As shown in Table 5, D1=DKK1, A2=CSGALNACT2, C1=CAV1, C4=CLIP4, T2=TFGB2, G6=GATA6iI, B1=BAMBI, D6=DNAJC6, N5E=NT5E, and G1=GULP1.

Quantitative methylation-specific PCR (QMSP). To selectively amplify hypermethylated promoter regions in genes of interest, probe and primers were designed using data from bisulfite sequencing of primary tumors which are complimentary only to bisulfite-converted sequences known to be methylated in tumor (see Tables 4A-4C). Primer combinations were validated using in vitro methylated and demethylated controls.

qRT-PCR. Total RNA was measured and adjusted to the same amount for each cell line, and then cDNA synthesis was performed using oligo-dt with the SUPERSCRIPT first-strand DNA synthesis kit (Invitrogen). The final cDNA products were used as the templates for subsequent PCR with primers designed specifically for each candidate gene. GAPDH was examined to ensure accurate relative quantitation in qRT-PCR. qRT-PCR heat maps were generated by median-normalization by gene, logged and heat maps generated using Excel.

Fifteen ovarian tumor samples, ten normal ovarian surface epithelium brushing samples, three normal ovarian cell lines, and three cancer cell lines (DAC treated and mock treated) were assayed for mRNA expression on the Affymetrix U133A mRNA expression microarray platform (16,383 probe sets) compiled from prior work and public sources of expression (oncomine.org). In order to select the best methylation biomarkers in ovarian cancer, all these criteria are combined using a score scheme, as follows:

down-regulation in cancer vs. normals: the results from the RankProd FDR analysis are used results are ranked, based on p-value; the score given to a probe reflects this ranking: Ranking Score=$\tan_{1-rank/54675}$ the FDR itself is taken into account: FDR Score=$\tan f(1-FDR)$ the fold change (FC) $\Delta$ is scored next, $\Delta_{max}$ being the maximal FC observed: FC Score=$\tan f(\Delta\Delta_{max})$; in other words, the tangens function of the ratio between delta and delta max.

the tangens function is chosen as all values are between 0 and 1, and the tangens between these values range from 0 to 1, 56 in a non-linear way, with somewhat (but not too extreme) more increase in score for values approaching 1 (being the best possible). This way, probes with a very good profile have a higher chance to acquire a high score and to be selected.

downregulation in cancer cell lines vs. normal cell lines and cancer cell lines vs. DAC-treated cancer cell lines is examined the same way low expression in tumor samples and cancer cell lines is examined as follows:

for every sample, the maximal expression is determined; for each probe its expression level is compared to the maximal expression level in that sample: expression score=1−probe expressionmaximal expression sample for all samples, the sum is calculated.

Using this score scheme, 11 values are generated (3 for down-regulation in tumors vs. normal; one for expression in tumor samples; 3 for down-regulation in cancer cell lines vs. normal cell line; one for low expression in cancer cell lines and three for upregulation after DAC treatment). For each of these values, the percentile of the probe is calculated: for each probe, for a specific score it is calculated where it is ranked, expressed in percentages versus the scores of all probes. For instance a probe with a score of 95% of a particular probe was situated at the top 5% probes with best scores. Next, we determine the number of scores where a probe was at least in the best 5% as well as the average percentile of all scores for this probe. The probes are sorted primary on the number of scores in the best 5% percentile, followed by the average percentile score. The sorting methodology allows to select a top-selection without having to choose thresholds or conditions. We chose to analyze the top 250 probes.

EXAMPLE 4

This example demonstrates how identification of tumor suppressor genes (TSGs) silenced by CpG methylation uncovers the molecular mechanism of tumorigenesis and potential tumor biomarkers.

Performing a pharmacologic unmasking technique, it was observed that GULP1, a molecule not previously related to cancer, is down-regulated in ovarian tumor tissues when compared to normal ovary cells. GULP1 is a cytoplasmic adaptor protein with a phosphotyrosine binding domain that plays a role in one of two partially redundant pathways that lead to the engulfment and clearance of apoptotic cells, according to several genetic studies performed in *Caenorhabditis elegans*. CED-2/CrkII, CED-5/Dock180, and CED-12/ELMO act together in one pathway that finalizes in the regulation of CED-10, which promotes cytoskeletal reorganization during engulfment of apoptotic cells. CED-1/MEGF10, CED-7/ABCA1, and CED-6/GULP collaborate together in the other pathway (11, 17-19), which at the end converge with the first pathway at CED-10 to mediate actin rearrangement and the subsequent engulfment.

An expression microarray was performed on 15 ovarian tumor samples, 10 ovarian normal surface epithelium, 3 ovarian cancer cell lines and 3 normal cell lines. All cells were treated with a demethylating agent that comprehensively uncovers genes silenced by promoter hypermethylation. The selection of the best candidates was based upon the differential expression between normal and tumor samples (or cell lines), them being downregulated in cancer when compared to normal, and finally the re-activation after the treatment with the demethylating agent.

One of the promising genes was GULP1, which expression pattern was then assessed by Reverse Transcriptase PCR and Western Blot and compared to its methylation status in the same six ovarian cell lines and showed correlation between absence of expression and presence of methylation (or the opposite situation).

Quantitative fluorogenic methylation specific PCR (QMSP) primers were then developed for GULP1. 437 ovarian tumor samples, 17 borderline tumors, 19 cystadenoma samples and 13 normal ovarian samples were profiled, finding 34.7% (151/437), 11.7% (2/17), 10.5% (2/19) and 0% (0/13) of methylation frequency, respectively (establishing an empiric cutoff). Using Fisher's exact test, a significant increase in methylation was observed when comparing tumors with cystadenomas and normals (p=0439 and p=0.0131, respectively). Late stage tumors also showed a higher frequency of methylation versus early stage (p=0.004).

TABLE 6

Demographic and clinical characteristics of ovarian cancer patients

| Characteristics | No. (%) patients |
|---|---|
| Age | |
| Median (range) | 61 (22-90) |
| Stage | |
| Early | 96 (25%) |
| Advanced | 288 (75%) |
| Chemotherapy Response | |
| Yes | 138 (35.9%) |
| No | 53 (13.8%) |
| Unknown/Not evaluable | 193 (50.3%) |
| EOC Histology | |
| Serous-papillary | 238 (62%) |
| Endometrioid | 38 (9.9%) |
| Mucinous | 43 (11.2%) |
| Clear Cell | 18 (4.7%) |
| Adeno | 14 (3.6%) |
| Other | 32 (8.3%) |
| Unknown | 1 (0.3%) |
| Deaths | |
| Yes (by the disease) | 208 (54.2%) |
| No | 161 (41.9%) |
| Unknown | 15 (3.9%) |
| Samples | |
| Tumor | 384 |
| Borderline | 17 |
| Cystadenoma | 19 |
| Normal | 16 |

So far, reduced log growth rates have been demonstrated after transiently overexpressing GULP1 in one ovarian cell, line (IGROVCP). These preliminary data indicate that GULP1 may be an ovarian cancer biomarker.

Although the invention has been described with reference to the above example, it will be understood that modifications and variations are encompassed within the spirit and scope of the invention. Accordingly, the invention is limited only by the following claims.

What is claimed is:

1. A method for determining a prognosis for ovarian cancer in a subject having ovarian cancer, for diagnosing ovarian cancer in a subject at risk of developing ovarian cancer, or for diagnosing a risk of developing ovarian cancer in a subject, comprising:
   a) obtaining a sample from the subject;
   b) detecting in nucleic acid in the sample from the subject a methylation state of at least three genes, or regulatory regions thereof, wherein the at least three genes include GULP1 and PGP9.5, and at least one additional gene selected from the group consisting of CSGALNACT2, HIC 1, AIM1, APC, PAK3, MCAM, MGMT, KIF1A, CCNA1, ESR1, SSBP2, GSTP1, FKBP4 and VGF, wherein said detecting comprises detecting hybridization of a probe to said nucleic acid and/or to amplification products of said nucleic acid, said probe consisting of the nucleotide sequence of SEQ ID NO: 33 and optionally a label or labels, and wherein said hybridization of said probe indicates that the methylation state of a regulatory region of GULP1 is hypermethylated;
   c) comparing the methylation state detected in (b) to that of a corresponding normal sample; and
   d) determining a diagnosis or prognosis based on (c), wherein the methylation state detected in (b) being hypermethylated in at least one of the three genes or regulatory regions thereof as compared to that of the corresponding normal sample is indicative of a poor prognosis in a subject having ovarian cancer, of the presence of ovarian cancer in a subject at risk of developing ovarian cancer, or of a risk of developing ovarian cancer in a subject.

2. The method of claim 1, wherein the sample is selected from the group consisting of a tissue sample, a frozen tissue sample, a biopsy specimen, a surgical specimen, a cytological specimen, whole blood, bone marrow, cerebral spinal fluid, peritoneal fluid, lymph fluid, serum, plasma, urine, stool, and nipple aspirate.

3. The method of claim 1, wherein the methylation state is of a CpG dinucleotide motif.

4. The method of claim 1, wherein the methylation state is of a CpG dinucleotide motif in a promoter.

5. The method of claim 1, further comprising detecting decreased expression of mRNA or protein encoded by at least one of the three genes.

6. The method of claim 1, further comprising detecting hypermethylation of at least one of the three genes or regulatory regions thereof by contacting at least a portion of the at least one gene or regulatory region with a methylation-sensitive restriction endonuclease, said endonuclease preferentially cleaving non-methylated recognition sites relative to methylated recognition sites, whereby cleavage of the portion indicates non-methylation of the portion provided that the at least one gene or regulatory region comprises a recognition site for the methylation- sensitive restriction endonuclease.

7. The method of claim 1, wherein detecting further comprises contacting at least a portion of at least one of the three genes or regulatory regions thereof with a chemical reagent that selectively modifies a non-methylated cytosine residue relative to a methylated cytosine residue, or selectively modifies a methylated cytosine residue relative to a non-methylated cytosine residue.

8. The method of claim 1, wherein detecting further comprises hybridization with at least one probe that hybridizes to a sequence comprising a modified non-methylated CpG dinucleotide motif but not to a sequence comprising an unmodified methylated CpG dinucleotide.

9. The method of claim 1, wherein detecting further comprises amplification with at least one primer that hybridizes to a sequence comprising a modified non-methylated CpG dinucleotide motif but not to a sequence comprising an unmodified methylated CpG dinucleotide motif thereby forming amplification products.

10. The method of claim 1, wherein detecting further comprises amplification with at least one primer that hybridizes to a sequence comprising an unmodified methylated CpG dinucleotide motif but not to a sequence comprising a modified non-methylated CpG dinucleotide motif thereby forming amplification products.

11. The method of claim 7, wherein the chemical reagent is hydrazine or comprises bisulfate ions.

12. A method for determining whether a subject is responsive to a particular therapeutic regimen comprising:
  a) obtaining a sample from the subject;
  b) detecting in nucleic acid in the sample from the subject the methylation state of at least three genes, or regulatory regions thereof, wherein the at least three genes include GULP1 and PGP9.5, and at least one additional gene selected from the group consisting of CSGALNACT2, HIC 1, AIM1, APC, PAK3, MCAM, MGMT, KIF1A, CCNA1, ESR1, SSBP2, GSTP1, FKBP4 and VGF, wherein said detecting comprises detecting hybridization of a probe to said nucleic acid and/or to amplification products of said nucleic acid, said probe consisting of the nucleotide sequence of SEQ ID NO: 33 and optionally a label or labels, and wherein said hybridization of said probe indicates that the methylation state of a regulatory region of GULP1 is hypermethylated;
  c) comparing the methylation state detected in (b) to that of a corresponding normal sample; and
  d) determining responsiveness to the therapeutic regimen, wherein the methylation state being hypermethylated in at least one of the three genes or regulatory regions thereof as compared with that of the normal sample is indicative of a subject who is non-responsive to the therapeutic regimen.

13. The method of claim 12, wherein the therapeutic regimen is administration of one or more chemotherapeutic agents.

14. The method of claim 13, wherein the one or more chemotherapeutic agents are administered in combination with a demethylating agent.

15. The method of claim 14, wherein the demethylating agent is 5-azacytidine, 5-aza-2-deoxycytidine or zebularine.

16. A method for identifying a cell that exhibits or is predisposed to exhibiting unregulated growth, comprising:
  detecting in the cell hypermethylation of at least three genes, or regulatory regions thereof, wherein the at least three genes include GULP 1 and PGP9.5, and at least one additional gene selected from the group consisting of CSGALNACT2, HIC1, AIM1, APC, PAK3, MCAM, MGMT, KIF1A, CCNA1, ESR1, SSBP2, GSTPI, FKBP4 and VGF, wherein said detecting comprises detecting hybridization of a probe to nucleic acid of said cell and/or to amplification products of said nucleic acid, said probe consisting of the nucleotide sequence of SEQ ID NO: 33 and optionally a label or labels, wherein said hybridization of said probe indicates that a regulatory region of GULP1 is hypermethylated, and wherein hypermethylation of at least one of said three genes or regulatory regions thereof is indicative of a cell that exhibits or is predisposed to exhibiting unregulated growth, thereby identifying the cell as exhibiting or being predisposed to exhibiting unregulated growth.

17. The method of claim 16, wherein the cell is an ovarian cancer cell.

18. The method of claim 16, wherein the hypermethylation is of a CpG dinucleotide motif.

19. The method of claim 16, wherein the hypermethylation is of a CpG dinucleotide motif in a promoter.

20. The method of claim 16, further comprising detecting decreased expression of mRNA or protein encoded by at least one of the three genes.

21. The method of claim 16, further comprising detecting hypermethylation of at least one of the three genes or regulatory regions thereof by contacting at least a portion of the at least one gene or regulatory region with a methylation-sensitive restriction endonuclease, said endonuclease preferentially cleaving non-methylated recognition sites relative to methylated recognition sites, whereby cleavage of the portion indicates non-methylation of the portion provided that the at least one gene or regulatory region comprises a recognition site for the methylation-sensitive restriction endonuclease.

22. The method of claim 16, wherein detecting further comprises contacting the cell with a chemical reagent that selectively modifies a non-methylated cytosine residue relative to a methylated cytosine residue, or selectively modifies a methylated cytosine residue relative to a non-methylated cytosine residue; and detecting a product generated by contacting the cell with the chemical reagent.

23. The method of claim 22, wherein detecting further comprises hybridization with at least one probe that hybridizes to a sequence comprising a modified non-methylated CpG dinucleotide motif but not to a sequence comprising an unmodified methylated CpG dinucleotide.

24. The method of claim 22, wherein detecting further comprises amplification with at least one primer that hybridizes to a sequence comprising a modified non-methylated CpG dinucleotide motif but not to a sequence comprising an unmodified methylated CpG dinucleotide motif thereby forming amplification products.

25. The method of claim 23, wherein detecting further comprises amplification with at least one primer that hybridizes to a sequence comprising an unmodified methylated CpG dinucleotide motif but not to a sequence comprising a modified non-methylated CpG dinucleotide motif thereby forming amplification products.

26. The method of claim 22, wherein the chemical reagent is hydrazine or comprises bisulfate ions.

* * * * *

SEQUENCE LISTING

<160> NUMBER OF SEQ ID NOS: 51

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
tggtgatgga ggaggtttag taagt        25

<210> SEQ ID NO 2
<211> LENGTH: 20
<212> TYPE: DNA
<213> ORGANISM: Artificial Sequence
<220> FEATURE:

<223> OTHER INFORMATION: Primer

<400> SEQUENCE: 2
cgcgggtatt ggatgttagt                                           20

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
gaaccaaaac gctccccat                                            19

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
tcgcggcgag tttattcg                                             18

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
ggcgttcgtt ttgggattg                                            19

<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
agttgcgcgg cgatttc                                              17

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
gttaggcggt tagggcgtc                                            19

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
gcgcgataaa ttagttggcg att                                       23

```
<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
agaatttagg tcggtttta tcg                                             23

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
cgaatatact aaaacaaccc gcg                                            23

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ttacggtcgt cgttattatc g                                              21

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
cggcgagtga gattgtaagg tt                                             22

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
atttttgcgg tcgtagcggt                                                20

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
ggatagcgtt cgtaggcg                                                  18

<210> SEQ ID NO 15
<211> LENGTH: 25
<212> TYPE: DNA
<213> ORGANISM: Artificial Sequence
<220> FEATURE:
<223> OTHER INFORMATION: Primer
```

```
<400> SEQUENCE: 15
gttcgtggtg acggtcggtt tcggg                                            25

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tgacgtttgt tatggtagcg                                                  20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ttagttgagg gtcgtggtcg                                                  20

<210> SEQ ID NO 18
<211> LENGTH: 30
<212> TYPE: DNA
<213> ORGANISM: Artificial Sequence
<220> FEATURE:
<223> OTHER INFORMATION: Probe

<400> SEQUENCE: 18
accaccaccc aacacacaat aacaaacaca                                       30

<210> SEQ ID NO 19
<211> LENGTH: 24
<212> TYPE: DNA
<213> ORGANISM: Artificial Sequence
<220> FEATURE:
<223> OTHER INFORMATION: Probe

<400> SEQUENCE: 19
gggagcgttg cggattattc gtag                                             24

<210> SEQ ID NO 20
<211> LENGTH: 22
<212> TYPE: DNA
<213> ORGANISM: Artificial Sequence
<220> FEATURE:
<223> OTHER INFORMATION: Probe

<400> SEQUENCE: 20
cccgtcgaaa acccgccgat ta                                               22

<210> SEQ ID NO 21
<211> LENGTH: 22
<212> TYPE: DNA
<213> ORGANISM: Artificial Sequence
<220> FEATURE:
<223> OTHER INFORMATION: Probe

<400> SEQUENCE: 21
cgttatggcg atgcggtttc gg                                               22

<210> SEQ ID NO 22
<211> LENGTH: 24
```

-continued

<212> TYPE: DNA
<213> ORGANISM: Artificial Sequence
<220> FEATURE:
<223> OTHER INFORMATION: Probe

<400> SEQUENCE: 22
cgataaaacc gaacgacccg acga                                              24

<210> SEQ ID NO 23
<211> LENGTH: 23
<212> TYPE: DNA
<213> ORGANISM: Artificial Sequence
<220> FEATURE:
<223> OTHER INFORMATION: Probe

<400> SEQUENCE: 23
cggtcgacgt tcggggtgta gcg                                               23

<210> SEQ ID NO 24
<211> LENGTH: 31
<212> TYPE: DNA
<213> ORGANISM: Artificial Sequence
<220> FEATURE:
<223> OTHER INFORMATION: Probe

<400> SEQUENCE: 24
caacatcgtc tacccaacac actctcctac g                                      31

<210> SEQ ID NO 25
<211> LENGTH: 27
<212> TYPE: DNA
<213> ORGANISM: Artificial Sequence
<220> FEATURE:
<223> OTHER INFORMATION: Probe

<400> SEQUENCE: 25
cctcccgaaa cgctaattaa ctacgcg                                           27

<210> SEQ ID NO 26
<211> LENGTH: 25
<212> TYPE: DNA
<213> ORGANISM: Artificial Sequence
<220> FEATURE:
<223> OTHER INFORMATION: Probe

<400> SEQUENCE: 26
acaatatcaa accgacgaca acgac                                             25

<210> SEQ ID NO 27
<211> LENGTH: 26
<212> TYPE: DNA
<213> ORGANISM: Artificial Sequence
<220> FEATURE:
<223> OTHER INFORMATION: Probe

<400> SEQUENCE: 27
aatcctcgcg atacgcaccg tttacg                                            26

<210> SEQ ID NO 28
<211> LENGTH: 28
<212> TYPE: DNA
<213> ORGANISM: Artificial Sequence
<220> FEATURE:
<223> OTHER INFORMATION: Probe

<400> SEQUENCE: 28

```
aaccaaaaaa aataaaaaat cacaaccg                                          28

<210> SEQ ID NO 29
<211> LENGTH: 28
<212> TYPE: DNA
<213> ORGANISM: Artificial Sequence
<220> FEATURE:
<223> OTHER INFORMATION: Probe

<400> SEQUENCE: 29
ttcggtcgta ttatttcgcg ttgcgtac                                          28

<210> SEQ ID NO 30
<211> LENGTH: 24
<212> TYPE: DNA
<213> ORGANISM: Artificial Sequence
<220> FEATURE:
<223> OTHER INFORMATION: Probe

<400> SEQUENCE: 30
atatccaaaa cgccgcgaaa ctcc                                              24

<210> SEQ ID NO 31
<211> LENGTH: 29
<212> TYPE: DNA
<213> ORGANISM: Artificial Sequence
<220> FEATURE:
<223> OTHER INFORMATION: Probe

<400> SEQUENCE: 31
gcgcccaaaa acgacgtaaa cctaaatac                                         29

<210> SEQ ID NO 32
<211> LENGTH: 27
<212> TYPE: DNA
<213> ORGANISM: Artificial Sequence
<220> FEATURE:
<223> OTHER INFORMATION: Probe

<400> SEQUENCE: 32
caaactacga aataacaata acgacgc                                           27

<210> SEQ ID NO 33
<211> LENGTH: 20
<212> TYPE: DNA
<213> ORGANISM: Artificial Sequence
<220> FEATURE:
<223> OTHER INFORMATION: Probe

<400> SEQUENCE: 33
cggcgggggg tcggtgagta                                                   20

<210> SEQ ID NO 34
<211> LENGTH: 23
<212> TYPE: DNA
<213> ORGANISM: Artificial Sequence
<220> FEATURE:
<223> OTHER INFORMATION: Probe

<400> SEQUENCE: 34
cgaacgctac ctaaaccccc gaa                                               23

<210> SEQ ID NO 35
<211> LENGTH: 27
<212> TYPE: DNA
<213> ORGANISM: Artificial Sequence
```

<220> FEATURE:
<223> OTHER INFORMATION: Primer

<400> SEQUENCE: 35
aaccaataaa acctactcct cccttaa                                        27

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
ccgacccacc tatacgaaaa                                                20

<210> SEQ ID NO 37
<211> LENGTH: 27
<212> TYPE: DNA
<213> ORGANISM: Artificial Sequence
<220> FEATURE:
<223> OTHER INFORMATION: Primer

<400> SEQUENCE: 37
ttatatgtcg gttacgtgcg tttatat                                        27

<210> SEQ ID NO 38
<211> LENGTH: 16
<212> TYPE: DNA
<213> ORGANISM: Artificial Sequence
<220> FEATURE:
<223> OTHER INFORMATION: Primer

<400> SEQUENCE: 38
ccgaccgcga caaacg                                                    16

<210> SEQ ID NO 39
<211> LENGTH: 19
<212> TYPE: DNA
<213> ORGANISM: Artificial Sequence
<220> FEATURE:
<223> OTHER INFORMATION: Primer

<400> SEQUENCE: 39
gccgacacgc gaactctaa                                                 19

<210> SEQ ID NO 40
<211> LENGTH: 22
<212> TYPE: DNA
<213> ORGANISM: Artificial Sequence
<220> FEATURE:
<223> OTHER INFORMATION: Primer

<400> SEQUENCE: 40
gccccaatac taaatcacga cg                                             22

<210> SEQ ID NO 41
<211> LENGTH: 19
<212> TYPE: DNA
<213> ORGANISM: Artificial Sequence
<220> FEATURE:
<223> OTHER INFORMATION: Primer

<400> SEQUENCE: 41
ccgggcgcct ccatcgtgt                                                 19

```
<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
ctcgacgact actctacgct at                                              22

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
acgcaaaatt cttctcccaa aa                                              22

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
gtattttttc gggagcgagg c                                               21

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
accgaaaatt ctacccttcg                                                 20

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
gaacgatcgc gaccaaataa atac                                            24

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
ttctacgaca aatctaacga a                                               21

<210> SEQ ID NO 48
<211> LENGTH: 22
<212> TYPE: DNA
<213> ORGANISM: Artificial Sequence
<220> FEATURE:
<223> OTHER INFORMATION: Primer
```

```
<400> SEQUENCE: 48
aaaaaccgaa ttccccaccc cg                                              22

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
atccgctacg cctacgacg                                                  19

<210> SEQ ID NO 50
<211> LENGTH: 18
<212> TYPE: DNA
<213> ORGANISM: Artificial Sequence
<220> FEATURE:
<223> OTHER INFORMATION: Primer

<400> SEQUENCE: 50
cggtggggaa atcgtgga                                                   18

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
cgcgtatttg ttagacgtgc g                                               21
```